(12) United States Patent
Fujioka et al.

(10) Patent No.: US 8,937,553 B2
(45) Date of Patent: Jan. 20, 2015

(54) SYRINGE DRIVE DEVICE AND SYRINGE DRIVE METHOD

(75) Inventors: Soichiro Fujioka, Osaka (JP); Tohru Nakamura, Osaka (JP); Osamu Mizuno, Osaka (JP); Akinobu Okuda, Nara (JP); Akihiro Ohta, Osaka (JP)

(73) Assignee: Panasonic Corporation, Osaka (JP)

( * ) Notice: Subject to any disclaimer, the term of this patent is extended or adjusted under 35 U.S.C. 154(b) by 128 days.

(21) Appl. No.: 13/575,391

(22) PCT Filed: Jan. 28, 2011

(86) PCT No.: PCT/JP2011/000495
§ 371 (c)(1),
(2), (4) Date: Jul. 26, 2012

(87) PCT Pub. No.: WO2011/093103
PCT Pub. Date: Aug. 4, 2011

(65) Prior Publication Data
US 2012/0299737 A1    Nov. 29, 2012

(30) Foreign Application Priority Data

Jan. 29, 2010  (JP) ................................ 2010-018148

(51) Int. Cl.
*G08B 21/00* (2006.01)
*A61M 5/145* (2006.01)
*A61M 5/168* (2006.01)

(52) U.S. Cl.
CPC ......... *A61M 5/1456* (2013.01); *A61M 5/16854* (2013.01); *A61M 5/1458* (2013.01); *A61M 2202/049* (2013.01); *A61M 2205/18* (2013.01);

(Continued)

(58) Field of Classification Search
USPC ......... 340/626, 438, 608, 611, 614, 588, 683, 340/686.6, 691.6, 687, 686.4, 456
See application file for complete search history.

(56) References Cited

U.S. PATENT DOCUMENTS 5,361,059 A * 11/1994 Hoffman et al. ............... 340/438
5,879,360 A *  3/1999 Crankshaw .................... 606/154

(Continued)

FOREIGN PATENT DOCUMENTS

JP    10-192402    7/1998
JP    2009-39311   2/2009

(Continued)

OTHER PUBLICATIONS

International Search Report issued Apr. 26, 2011 in International (PCT) Application No. PCT/JP2011/000495.
English translation of the International Preliminary Report on Patentability issued Sep. 18, 2012 in International (PCT) Application No. PCT/JP2011/000495.

(Continued)

*Primary Examiner* — Daniel Previl
(74) *Attorney, Agent, or Firm* — Wenderoth, Lind & Ponack, L.L.P.

(57) ABSTRACT

A syringe drive device 11 includes a fixing section 15 fixing an outer tube 14, a movable holder 16 holding a plunger 13, and a drive section 42 driving the holder 16 along an axis of the plunger to push and pull the plunger with respect to the outer tube 14. An internal pressure detector 18 has a positive pressure detection switch 63 detecting an internal pressure of a syringe 12. A determination section 41 determines the issuance of an alert when the holder 16 is stopped and the positive pressure detection switch 63 is ON. A display section 19 is lit to indicate the alert when the determination section 41 determines to issue the alert.

8 Claims, 20 Drawing Sheets

(52) U.S. Cl.
CPC .. *A61M 2205/332* (2013.01); *A61M 2205/3331* (2013.01)
USPC ............... 340/626; 340/686.4; 340/438

(56) References Cited

U.S. PATENT DOCUMENTS

| 6,533,757 | B1* | 3/2003 | Lampropoulos et al. | ..... 604/131 |
| 7,611,488 | B2* | 11/2009 | Chang | ............ 604/110 |
| 8,209,060 | B2* | 6/2012 | Ledford | ........ 700/282 |
| 2011/0184383 | A1* | 7/2011 | Hasegawa | ............ 604/506 |

FOREIGN PATENT DOCUMENTS

| WO | 2008/001881 | 1/2008 |
| WO | 2008/063429 | 5/2008 |

OTHER PUBLICATIONS

Japanese Office Action (OA) mailed Jan. 7, 2014 in corresponding Japanese Patent Application No. 2011-551781.

Chinese Office Action mailed Aug. 4, 2014 in corresponding Chinese Patent Application No. 20118007456.5 (with English translation).

* cited by examiner

SYRINGE DRIVE DEVICE AND SYRINGE DRIVE METHOD

TECHNICAL FIELD

The present invention relates to a syringe drive device for driving a syringe by pushing and pulling a plunger of the syringe.

BACKGROUND ART

In cases of performing medicinal solutions mixing operations in hospitals, such as preparing infusion medicinal solutions, it has been well known that a plurality of medicinal solutions filled respectively in medicine bottles called vials are aspirated by means of a syringe and are mixed in this syringe to prepare the infusion medicinal solutions. The medicinal solutions thus prepared are then discharged from the syringe so as to be filled into an infusion bag or the like.

In such medicinal solution mixing operations performed in hospitals, there are cases where a large amount of a medicinal solution of high viscosity, such as dextrose in water in high concentration, is dispensed using a syringe of a large content of about 50 ml, for example. In these cases, quite a large force of more than one hundred N is needed for driving the syringe by pushing and pulling a plunger. The medicinal solutions to be prepared may include one that is carcinogenic and harmful to healthy people, such as a carcinostatic agent, which needs to be handled with extreme care. Accordingly, it is quite a workload for an operator to handle a syringe in order to mix medicinal solutions.

There has been proposed, as a device assisting in operating a syringe, a syringe drive device that is used for injecting a medicinal solution into a human body at a constant quantity, for example. A syringe drive device of this type generally includes a fixing section that holds a flange of an outer tube of a syringe to fix the syringe, and a holder that holds a brim section of a plunger so as to axially move the plunger with respect to the syringe fixed to the fixing section. Further, a pressure detector provided at the holder detects an internal pressure of the syringe in accordance with a force for axially moving the plunger, so as to indicate a signal corresponding to the detected internal pressure to an operator (refer to JP 1998-192402 A).

FIG. 14 is a view showing a configuration of a conventional syringe drive device disclosed in JP 1998-192402 A. In this syringe drive device, rotation of a motor is converted to linear motion of a holder 1, and a plunger receiver 4 of the holder 1 pushes a brim section 3 of a plunger 2, so that a medicinal solution in a syringe 5 is discharged. A holder arm 6 presses the brim section 3 of the plunger 2 against the plunger receiver 4. There is further provided a pressure sensor 7 between the plunger receiver 4 and the holder 1 with a pressure transmission portion 8 being interposed therebetween. By indicating a signal corresponding to a detection value of the pressure sensor 7 in the case where the brim section 3 is pressed, an alert is issued indicating blockage in a route of an infusion solution or disengagement of the syringe. More specifically, an alert is issued indicating blockage when the detected pressure is too large. On the other hand, an alert is issued indicating disengagement of the syringe when the detected pressure is too small. This configuration allows an operator to recognize a malfunction and deal with it promptly if the operator has performed any unintended operation on the syringe, which therefore realizes safe operation of the syringe.

SUMMARY OF THE INVENTION

Technical Problem

Such a syringe drive device has a problem in that the pressure is varied in accordance with the type of medicinal solution and discharge speed, and a very small internal pressure of the syringe cannot be detected, as the internal pressure of the syringe is detected under the influence of viscous resistance of the medicinal solution, which is as large as more than one hundred N. For example, it is impossible to alert an operator in advance to medicinal solution aerosolization that occurs at a syringe internal pressure of about 5 kPa. The medicinal solution aerosolization refers to a phenomenon that, upon extracting a syringe from a vial in an operation of mixing injection drugs, a medicinal solution spatters if the syringe has an internal pressure higher (positive pressure) than the peripheral pressure. If a medicinal solution harmful to healthy people, such as a carcinostatic agent, is spattered due to medicinal solution aerosolization, the health of the operator may be affected by adhesion or aspiration of the spattered substance.

In conventional cases where an operator manually mixes injection drugs, the operator senses the internal pressure of a syringe by feeling with a hand. It will be possible for an operator to detect, by feeling with a hand based on experiences and the like, a very small internal pressure of the syringe at which level medicinal solution aerosolization occurs. However, with use of the syringe drive device described above, which reduces the workload of an operator, it is difficult to sense the internal pressure of a syringe by feeling with a hand.

In the syringe drive device shown in FIG. 14, the pressure sensor 7 is provided between the plunger receiver 4 and the holder 1. Accordingly, it is possible to roughly calculate the internal pressure of the syringe in accordance with the force applied to the plunger receiver 4. In order to detect a malfunction occurring while the syringe is driven and alert an operator, calculation of the internal pressure of the syringe as well as indication of alerts to the operator are performed constantly. Nevertheless, the medicinal solution aerosolization occurs at a very small threshold for a syringe internal pressure. The force applied to the plunger 2 due to the syringe internal pressure of about +5 kPa is at a level to be cancelled by viscous resistance of a medicinal solution while the syringe is being driven. It is thus difficult to accurately detect a very small internal pressure of the syringe 5 even by detecting the force applied to the plunger receiver 4 by means of the pressure sensor 7, which results in difficulty in alerting the operator in advance to the occurrence of medicinal solution aerosolization.

The present invention has been made to solve these problems, and an object thereof is to provide a syringe drive device that allows an operator to recognize in advance the occurrence of medicinal solution aerosolization. The present invention also provides a method of controlling the syringe drive device.

Solutions to the Problems

According to a first aspect of the present invention, there is provided a syringe drive device including: a fixing section fixing an outer tube of a syringe; a movable holder holding a plunger of the syringe; a drive section driving the holder along an axis of the plunger to push and pull the plunger with respect to the outer tube; an internal pressure detector detecting an internal pressure of the syringe; an operation detector detecting whether the holder is driven or stopped; a determination section determining the issuance of an alert when the operation detector detects that the holder is stopped and the internal pressure of the syringe detected by the internal pressure detector is not less than a predetermined alert value; and a display section indicating the alert when the determination section determines to issue the alert.

The alert value corresponds to the internal pressure of the syringe (in a range from 0 KPa to 5 KPa, for example) at which level medicinal solution aerosolization occurs. Therefore, an operator can recognize, by means of the alert indicated by an alerting portion, that the internal pressure of the syringe is increased to a level where medicinal solution aerosolization possibly occurs.

The internal pressure detector includes: a movable section that is supported by the holder so as to be movable along the axis of the plunger and is in contact with a brim section of the plunger; and an elastically biasing portion elastically biasing the movable section so as to push the plunger and pressing the movable section against the brim section of the plunger. The internal pressure detector further includes a switch to be turned ON when a force for pressing the movable section so as to pull the plunger by means of the brim section of the plunger is not less than a magnitude corresponding to the alert value, or a force detector detecting the force for pressing the movable section so as to pull the plunger by means of the brim section of the plunger. In particular, a force for pressing the plunger so as to be pushed by means of the movable section using a bias force of the elastically biasing portion is preferably set not to be less than a static frictional force between the syringe and the plunger.

In this configuration, it is possible to eliminate or reduce the influence of the frictional force between the syringe and the plunger, thereby to improve accuracy in detection of the internal pressure of the syringe. Because whether or not to issue an alert is determined in accordance with the internal pressure of the syringe detected with a high degree of accuracy, it is possible improving the accuracy of the alert to medicinal solution aerosolization.

According to a second aspect of the present invention, there is provided a method of controlling a syringe drive device that includes an outer tube fixing section fixing an outer tube of the syringe, a holder holding a plunger of the syringe, and a drive section driving the holder along an axis of the plunger to push and pull the plunger with respect to the outer tube, and the method includes: detecting whether the holder is driven or stopped; detecting an internal pressure of the syringe when the holder is stopped; and issuing an alert when the internal pressure of the syringe is not less than an alert value.

Effect of the Invention

The syringe drive device and the method of controlling the syringe drive device according to the present invention alert an operator in advance to occurrence of a medicinal solution aerosolization, which achieves a safe operation of mixing injection drugs. In particular, because the movable section is provided so as to be elastically biased to the plunger of the syringe, it is possible to improve accuracy in detection of a very small internal pressure of the syringe, resulting in that an operator can be alerted to the occurrence of medicinal solution aerosolization with a higher degree of accuracy.

DESCRIPTION OF THE EMBODIMENTS

Embodiments of the present invention are described below with reference to the drawings. It is noted that the same components are denoted by the same reference signs, and description thereof will not be repetitively provided where appropriate.

First Embodiment

Figure 1:
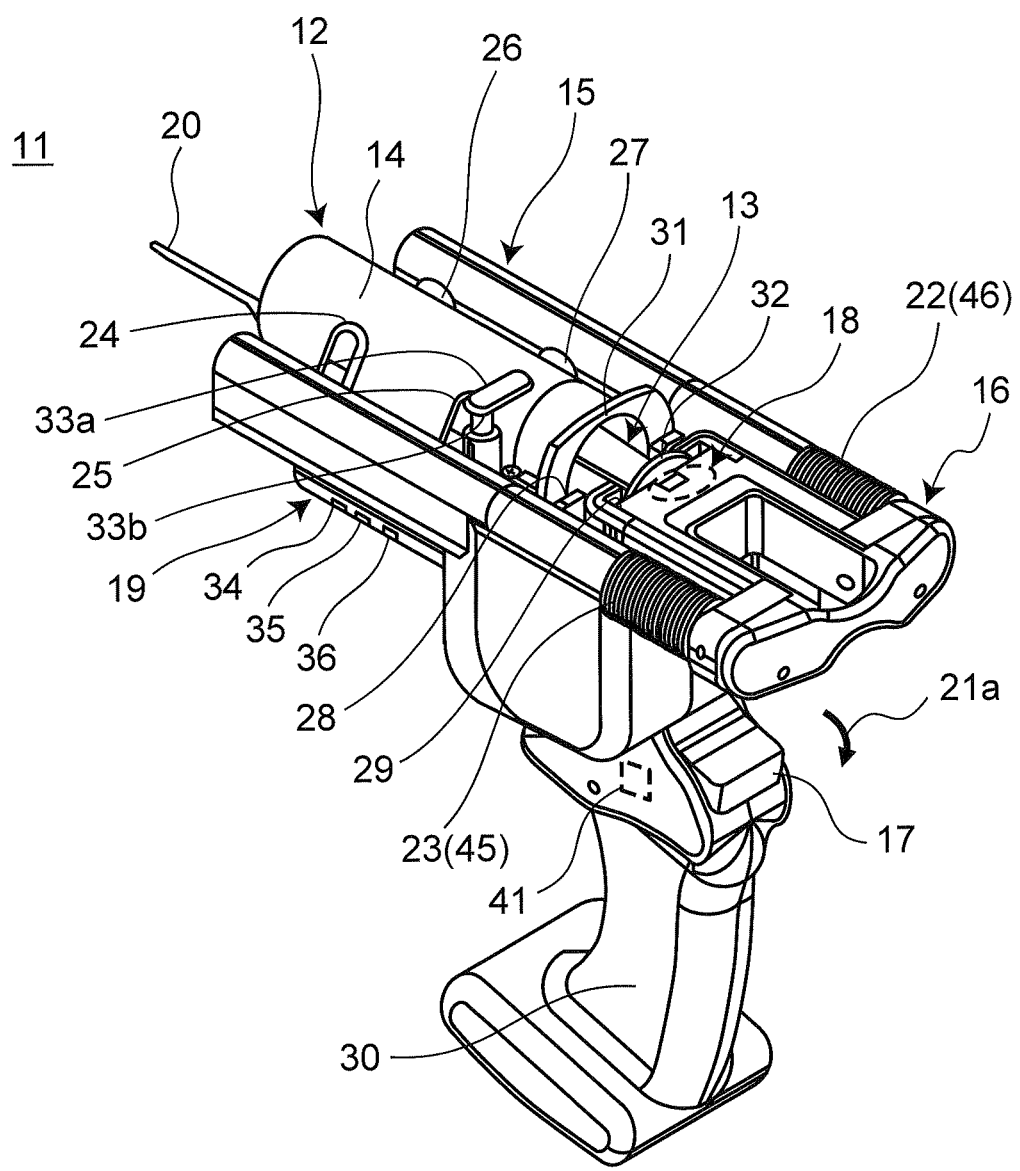
FIG. 1 is a perspective view of a syringe drive device according to a first embodiment of the present invention.
Figure 2:
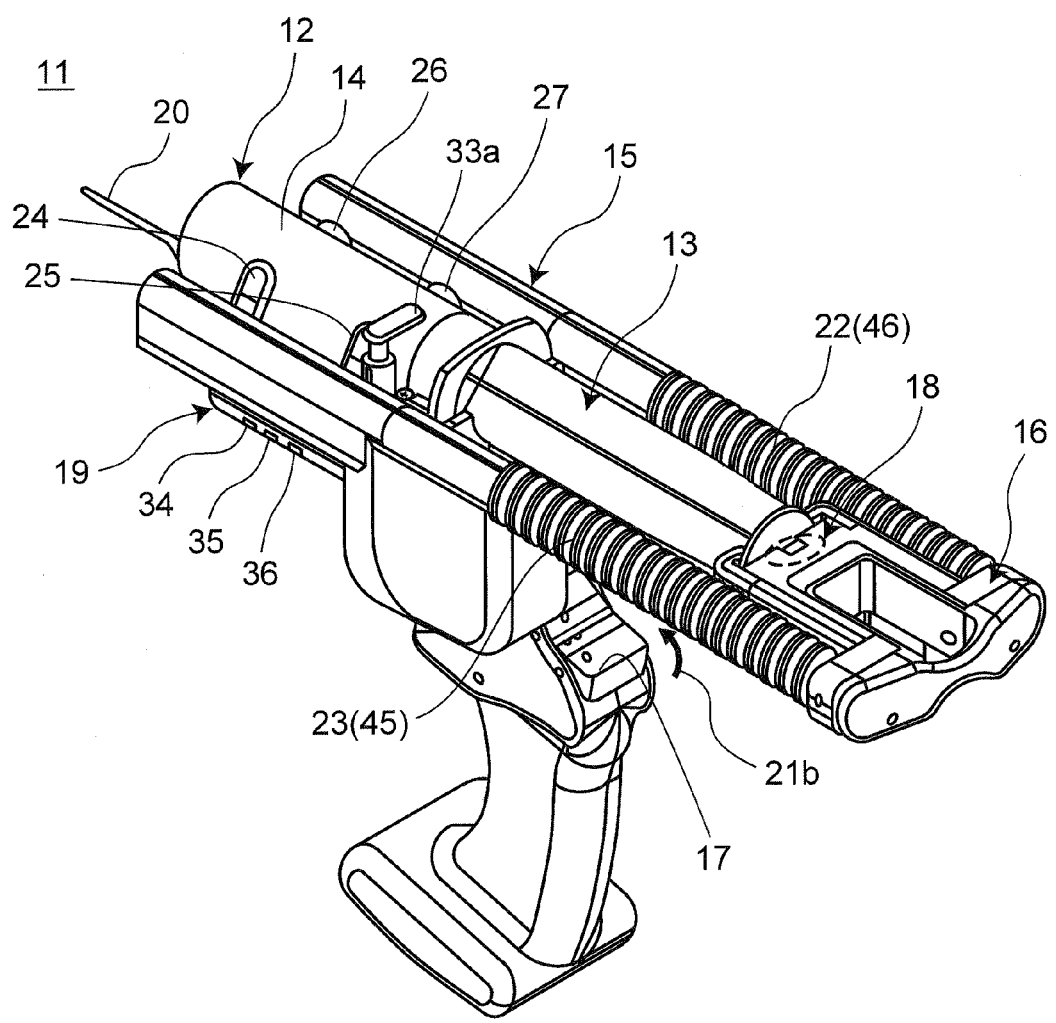
FIG. 2 is a perspective view of the syringe drive device according to the first embodiment in an extended state.
Figure 3:
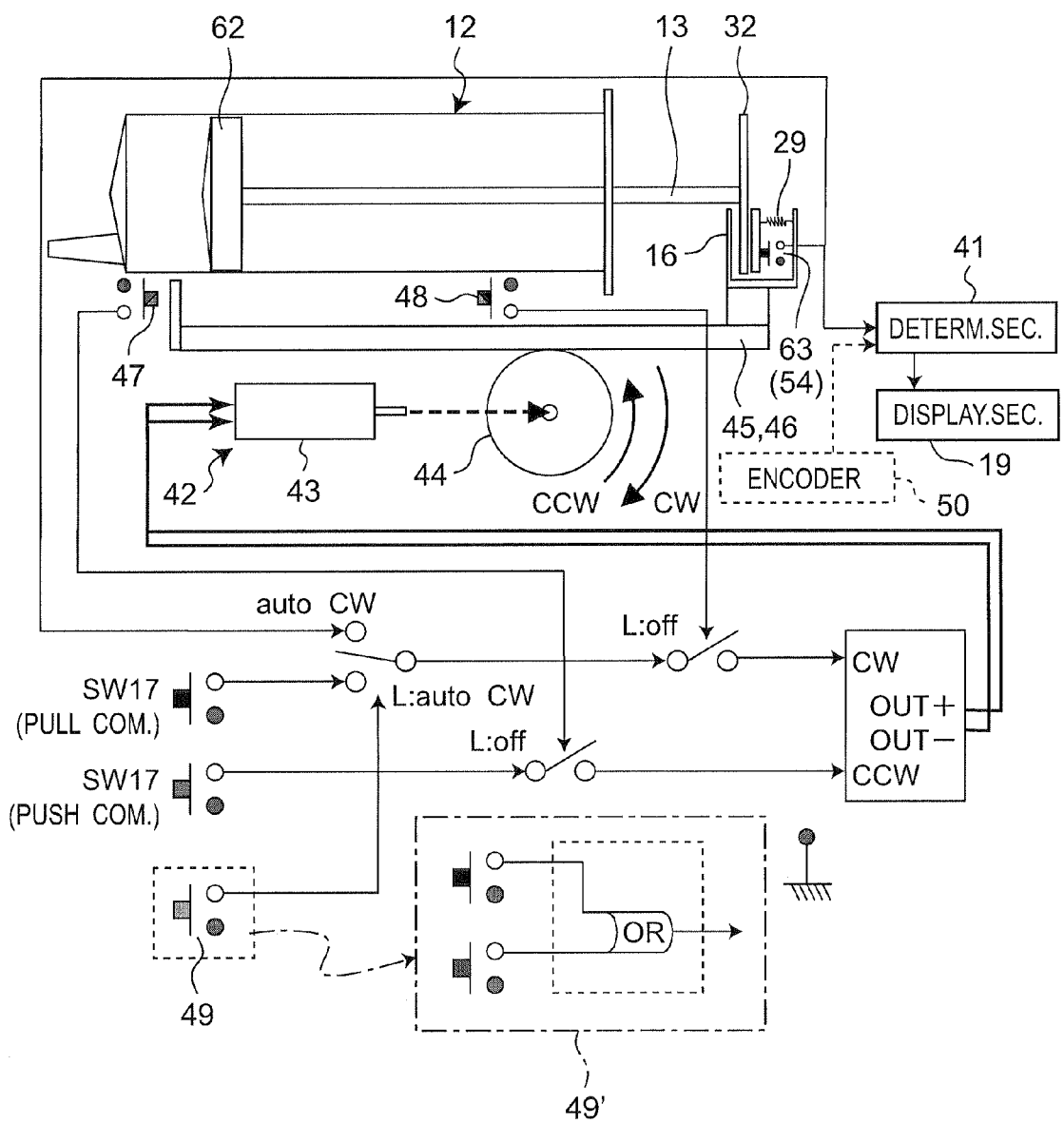
FIG. 3 is a block diagram of the syringe drive device according to the first embodiment.
Figure 4:
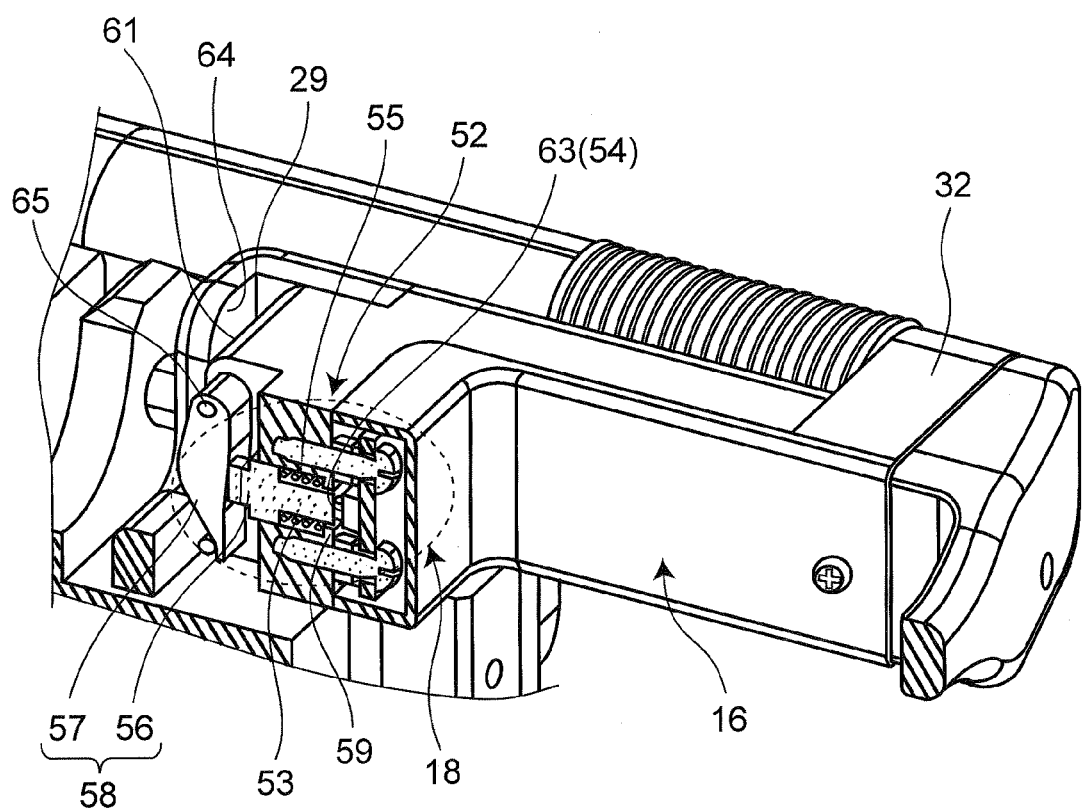
FIG. 4 is a perspective view of a holder according to the first embodiment of the present invention, in which the holder is partially shown in cross section.

FIGS. 1 to 3 each show a syringe drive device 11 according to the present first embodiment. The syringe drive device 11 assists in pushing and pulling a plunger 13 of a syringe 12 with respect to an outer tube 14.

The syringe drive device 11 includes a fixing section 15 that fixes the outer tube 14 of the syringe 12, a holder 16 that holds the plunger 13 of the syringe 12, and a drive section 42 (shown in FIG. 3 as a pattern view) which linearly moves the holder 16 along an axis of the plunger 13. The fixing section 15 is provided therebelow with a grip section 30 that extends downward and is to be held by an operator with a hand.

The syringe 12 is mounted on the fixing section 15 of the syringe drive device 11 such that a flange 31 of the outer tube 14 is fitted in a recess of a flange accommodation section 28 and a press section (brim section) 32 provided at an end of the plunger 13 is fitted in a recess 29 provided in a front portion of the holder 16. Then, a shaft section 33b of a lever 33a is pressed to be inserted. In conjunction therewith, retainers 24, 25, 26, and 27 are brought into operation to hold the outer tube 14. When the shaft section 33b is pressed to be inserted and then the lever 33a is rotated, motion of the shaft section 33b is restricted and the retainers 24, 25, 26, and 27 are locked in the state of holding the outer tube 14. Accordingly, the syringe 12 is fixed to the fixing section 15 of the syringe drive device 11.

As shown in FIG. 3 as a pattern view, the drive section 42 includes a motor 43 functioning as a drive source, a gear 44 functioning as a transmission mechanism, and paired racks 45 and 46 that convert rotation of the gear 44 to linear movement. These racks 45 and 46 have rear ends respectively coupled to the holder 16, so that the holder 16 moves in a direction corresponding to the direction of rotation of the motor 43. When the holder 16 moves along the axis of the syringe, the plunger 13 is pushed or pulled with respect to the outer tube 14 that is fixed to the fixing section 15.

When the racks 45 and 46 move forward and the holder 16 moves so as to come close to the fixing section 15, the plunger 13 of the syringe 12 fixed to the fixing section 15 moves so as to be pushed toward the outer tube 14 (see FIG. 1). As conceptually shown in FIG. 3, there is provided a start point detection sensor 47 that detects the holder 16 being located at a start point. When the plunger 13 is pushed to the limit toward the outer tube 14, the holder 16 is located at the start point.

When the racks 45 and 46 move backward and the holder 16 moves so as to be away from the fixing section 15, the plunger 13 of the syringe 12 fixed to the fixing section 15 moves so as to be pulled out of the outer tube 14 (see FIG. 2). As conceptually shown in FIG. 3, there is provided an end point detection sensor 48 that detects the holder 16 being located at an end point. When the plunger 13 is pulled to the limit out of the outer tube 14, the holder 16 is located at the end point.

The rear portions of the racks 45 and 46 are accommodated in stretchable sections 22 and 23 that are each configured as a cover in a bellows shape. As shown in FIGS. 1 and 2, the racks 45 and 46 are always covered with the stretchable sections 22 and 23 even when the holder 16 linearly moves along the axis of the plunger 13.

The syringe drive device 11 includes an operation switch 17 that is located at an upper rear position of the grip section 30 and functions as an operation portion sending an operation command to the drive section 42 provided at the holder 16. The syringe drive device 11 also includes a main power switch (not shown) at the fixing section 15. The syringe drive device 11 further includes a mode switch 49 (conceptually shown only in FIG. 3) which is used for selecting whether or not to execute an automatic mode to be detailed later. In place of the mode switch 49, there may be adopted a circuit 49' that commands the automatic mode upon detection of the operation switch 17 being in a neutral position (in the case where both a pull command and a push command are OFF).

When the operation switch 17 sends an operation command to pull the plunger 13 (aspiration command), a positive current flows into the motor 43 of the drive section 42 to cause positive rotation (conceptually indicated by an arrow CW in FIG. 3). In this case, the holder 16 as well as the racks 45 and 46 move backward so as to be away from the fixing section 15. As a result, the plunger 13 is pulled out the outer tube 14 of the syringe 12 that is fixed to the fixing section 15, and a medicinal solution and air are aspirated into the syringe 12 through an injection needle 20. On the other hand, when the operation switch 17 sends an operation command to push the plunger 13 (discharge command), a negative current flows into the motor 43 of the drive section 42 to cause negative rotation (conceptually indicated by an arrow CCW in FIG. 3). In this case, the holder 16 as well as the racks 45 and 46 move forward so as to come close to the fixing section 15. As a result, the plunger 13 is pushed into the outer tube 14 of the syringe 12 that is fixed to the fixing section 15, and a medicinal solution and air are discharged from the syringe 12 through the injection needle 20.

The operation switch 17 is assumed to be operated with a thumb. The pull command (aspiration command) is sent if the portion close to an operator in the operation switch 17 is pressed (in the direction indicated by an arrow 21a). On the other hand, the push command (discharge command) is sent if the far portion is pressed (in the direction indicated by an arrow 21b). In this manner, the direction in which the thumb moves in order to operate the operation switch 17 is the same as the direction in which the holder 16 (the plunger 13) moves. Accordingly, the operator can easily recognize an operation of the operation switch 17 and behavior of the syringe drive device 11 (either aspirating or pushing). The operation switch 17 returns to the neutral position when the finger is detached from the operation switch 17. The operation command is cancelled when the operation switch 17 returns to the neutral position. Accordingly, supply of a current to the motor 43 is stopped thereby to stop the stretchable sections 22 and 23, with a result that movement of the holder 16 is stopped.

The syringe drive device 11 includes an internal pressure detector 18 provided at the holder 16, a determination section 41 mounted in the fixing section 15, and a display section 19 provided on a side surface of the fixing section 15.

The internal pressure detector 18 detects a force applied to the plunger 13 due to the internal pressure of the syringe 12. The internal pressure detector 18 according to the present embodiment detects the internal pressure of the syringe 12 as an ON/OFF state of a positive pressure detection switch 63, which is to be described later. The internal pressure detector 18 will be detailed later with regard to its structure and functions.

If the internal pressure of the syringe 12 detected by the internal pressure detector 18 is not less than a predetermined alert value (if the positive pressure detection switch 63 is ON in the present embodiment, as to be described later), the determination section 41 determines issue of an alert indicating that occurrence of medicinal solution aerosolization is highly possible. Medicinal solution aerosolization refers to a phenomenon that, upon extracting a syringe from a vial in an operation of mixing injection drugs, a medicinal solution spatters if the syringe has an internal pressure higher (positive pressure) than the peripheral pressure.

The alert value is preferably set to an ordinary threshold (about +5 kPa) of an internal pressure of a syringe, at which level medicinal solution aerosolization occurs. To be more reliable, the alert value may be set to be smaller than the ordinary threshold (such as a positive value close to 0 kPa). This setting enables an alert to be issued in a case where the syringe 12 has a positive internal pressure. Therefore, an operator can be reliably alerted in advance to a dangerous state where medicinal solution aerosolization may occur with high possibility. The alert value may be set in a range from 0 kPa to 5 kPa, for example.

The display section 19 functions as an alerting portion that issues an alert to inform an operator of highly possible occurrence of medicinal solution aerosolization in accordance with the result of determination made by the determination section 41.

In the syringe drive device 11 according to the present embodiment, the display section 19 has three LEDs 34, 35, and 36, as shown in FIGS. 1 and 2. The LED 34 is in green, which is lit when the main power is ON and is unlit when the main power is OFF. The LED 35 is in orange, and is lit in a case where the start point detection sensor 47 detects that the holder 16 is located at the start point (the plunger 13 is pushed to the limit toward the outer tube 14). The LED 35 is lit also in a case where the end point detection sensor 48 detects that the holder 16 is located at the end point (the plunger 13 is pulled to the limit out of the outer tube 14).

The LED 36 is in red, and indicates the result of determination made by the determination section 41. More specifically, the LED 36 is lit in a case where determination on issue of an alert is established by the determination section 41 (where the internal pressure of the syringe 12 detected by the internal pressure detector 18 is not less than the alert value). The LED 36 is unlit in a case where determination on issue of an alert is not established by the determination section 41.

The alert to be indicated by the alerting portion (the display section 19 according to the present embodiment) is not limited to a visual mode such as lighting of an LED, but may be in any other mode as long as an operator can reliably recognize issue of an alert. For example, a vibrator such as a vibrating motor may be buried in the grip section 30, so that the vibrator vibrates in the case where determination on issue of an alert is established by the determination section 41. In this case, the operator can notice possibility of occurrence of medicinal solution aerosolization by such vibration even if the operator fails to look at the display section 19. If the fixing section 15 and the grip section 30 are provided separately from each other, vibration of the vibrator is attenuated so as not to transfer strong vibration to the syringe 12. Alternatively, there may be provided a vibration-free material, such as rubber, between the fixing section 15 and the grip section 30. The alert indicated by the alerting portion may include an acoustic element such as a buzzer sound.

Only in a case where the holder 16 is stopped (where the holder 16 is not moving so as to push or pull the plunger), the determination section 41 commands the display section 19 to light the LED 36 (indicate an alert) when the detection value of the internal pressure of the syringe 12 is not less than the alert value and determination on issue of an alert is established. Accordingly, if the holder 16 is being driven and the plunger 13 is moving to suck or discharge a medicinal solution, the LED 36 is unlit regardless of the internal pressure of the syringe 12. This is because the syringe 12 is extracted only when a medicinal solution is not aspirated or discharged, and no alert needs to be issued during these operations. Moreover, in a case where no alert is issued while a medicinal solution is aspirated or discharged, the operator can concentrate only on operating the syringe even in the syringe operation of dealing with a carcinostatic agent, in which case extreme care is required. Furthermore, the syringe drive device 11 realizes more accurate issue of an alert to danger of occurrence of medicinal solution aerosolization by not being influenced by viscous resistance of the medicinal solution.

The determination section 41 according to the present embodiment constantly determines whether or not the internal pressure of the syringe 12 detected by the internal pressure detector 18 is not less than the alert value, and the display section 19 indicates the result only in the case where the holder 16 is stopped. Alternatively, if focusing only on occurrence of medicinal solution aerosolization while the holder 16 is stopped, the determination section 41 may perform determination only when the holder 16 is stopped.

There may be provided an encoder 50 that detects rotation of the motor 43, in order to determine whether the holder 16 is driven (in the state where the drive section 42 moves the holder 16 so as to push or pull the plunger) or stopped. In this case, the determination section 41 detects the state of rotation of the motor 43 in accordance with an input signal from the encoder 50. In accordance with the result of detection, the determination section 41 determines whether the holder 16 is driven or stopped. In other words, in this case, the encoder 50 and the determination section 41 configure an operation detector that detects whether the holder 16 is driven or stopped. The motor is definitely rotating while the holder 16 moves. On the other hand, the motor is definitely stopped while the holder 16 is stopped. Accordingly, it is possible to reliably determine whether or not the holder 16 is stopped by detection of the state of rotation of the motor 43 by means of the encoder 50. Instead of detection of the state of rotation by means of the encoder 50, whether or not the holder 16 is stopped may be determined in accordance with a regenerative current of the motor 43.

If the gear 44 of the drive section 42 is configured to have a high reduction ratio and low reverse mobility (such that, even if a force is applied to the holder 16, the motor 43 receives only a small force according to the reduction ratio), the motor 43 is not rotated and the holder 16 also does not move. In this configuration, when the operation switch 17 does not send an operation command and no current flows to the motor 43, the holder 16 can be stopped even though an external force is applied. This configuration enables determination regarding whether or not the holder 16 is stopped only in accordance with an operation command of the operation switch 17. Accordingly, the stopped state of the holder 16 can be detected at a lower cost. The determination section 41 according to the present embodiment determines that the holder 16 is stopped when the operation switch 17 is not set to send the pull command or the push command but is in the neutral position (step S1 in FIG. 7A). In other words, in the present embodiment, the operation switch 17 and the determination section 41 configure the operation detector that detects whether the holder 16 is driven or stopped.

Generally described below is a method of operating the syringe drive device 11. The operator initially holds the grip section 30 and attaches the syringe 12 to the syringe drive device 11 thus held. Then, the operator inserts the injection needle 20 provided at a distal end of the syringe 12 into a vial (not shown).

In order to suck a medicinal solution from the vial into the syringe 12, the main power switch (not shown) is turned ON and then the operation switch 17 is pressed in the direction indicated by the arrow 21a with a thumb, so as to send the aspiration operation command to the syringe drive device 11. By these operations, the holder 16 is linearly moved so as to be away from the plunger 13, which is pulled out of the outer tube 14, with a result that the medicinal solution in the vial is aspirated into the syringe 12. The finger is detached from the operation switch 17 after the medicinal solution of a sufficient amount is aspirated into the syringe 12. Then, the operation switch 17 returns to the neutral position and the holder 16 is stopped. When the operation switch 17 is pressed in the direction indicated by the arrow 21b with the thumb to send the discharge operation command to the syringe drive device 11, the holder 16 linearly moves so as to come close to the plunger 13, which is pushed toward the outer tube 14, with a result that the medicinal solution is discharged from the injection needle 20 into the vial. In this manner, the operator can mix medicinal solutions with use of the syringe drive device 11, by pushing and pulling the plunger 13.

For discharging a medicinal solution into a vial, an air exchange operation of adjusting the internal pressure of the syringe 12 is performed in order to prevent occurrence of medicinal solution aerosolization described earlier. The injection needle 20 is initially inserted into the vial and a small volume of air, for example, is aspirated from the vial into the syringe 12. Thereafter, the medicinal solution is discharged into the vial by repeating the air exchange operation of discharging the medicinal solution of substantially the same amount from the syringe 12 into the vial.

In this operation of discharging a medicinal solution, if the amount of the medicinal solution and the amount of air exchanged are not well balanced, the internal pressure of the vial or the syringe 12 is raised. Medicinal solution aerosolization will inevitably occur if the injection needle 20 is extracted in a state where the internal pressure of the syringe 12 is not less than the threshold for occurrence of medicinal solution aerosolization. However, in the syringe drive device 11 according to the present embodiment, the LED 36 of the display section 19 is lit if the determination section 41 determines that the detection value of the internal pressure of the syringe 12 is not less than the alert value while the holder 16 is stopped. More specifically, the operator is alerted by lighting of the LED 36 to the state where medicinal solution aerosolization will occur with high possibility by extracting the needle from the vial and therefore the injection needle should not be extracted from the vial. On the other hand, the LED 36 is unlit when the detection value is less than the alert value, so as to inform the operator that medicinal solution aerosolization is less likely to occur and therefore the needle can be extracted. Therefore, the operator looks at the LED 36 to find a timing of extracting the syringe 12 where medicinal solution aerosolization occurs with low possibility.

Detailed next is the internal pressure detector 18 with reference to FIGS. 4 to 6E.

A frictional force (hereinafter, referred to as a syringe frictional force) is applied between a gasket 62 (see FIGS. 8A and 8B) provided at a distal end of the plunger 13 and the outer tube 14 of the syringe 12. In a case where the syringe 12 has a small diameter and a small content, the syringe frictional force may largely influence the internal pressure of the syringe 12 to be detected by the internal pressure detector 18 (see FIG. 4). Even if the syringe frictional force has a large influence, the internal pressure detector 18 according to the present embodiment eliminates such an influence of the syringe frictional force so as to enable detection of the internal pressure of the syringe 12 with a high degree of accuracy and thereby improves the accuracy in determining the issuance of an alert by the determination section 41.

Figure 6A:
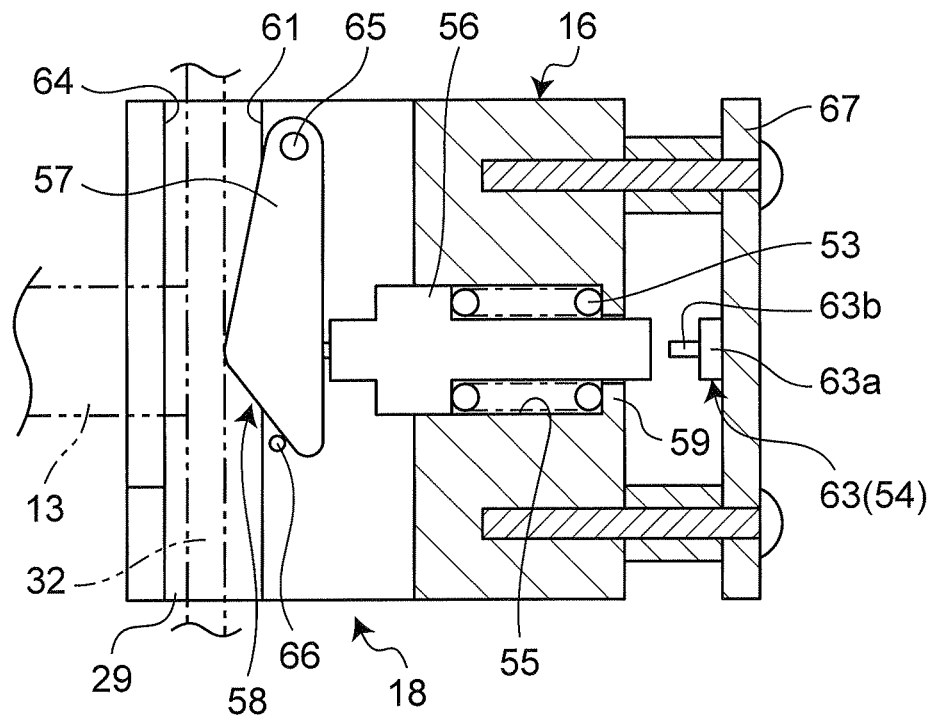
FIG. 6A is a sectional pattern view of the holder according to the first embodiment.
Figure 6B:
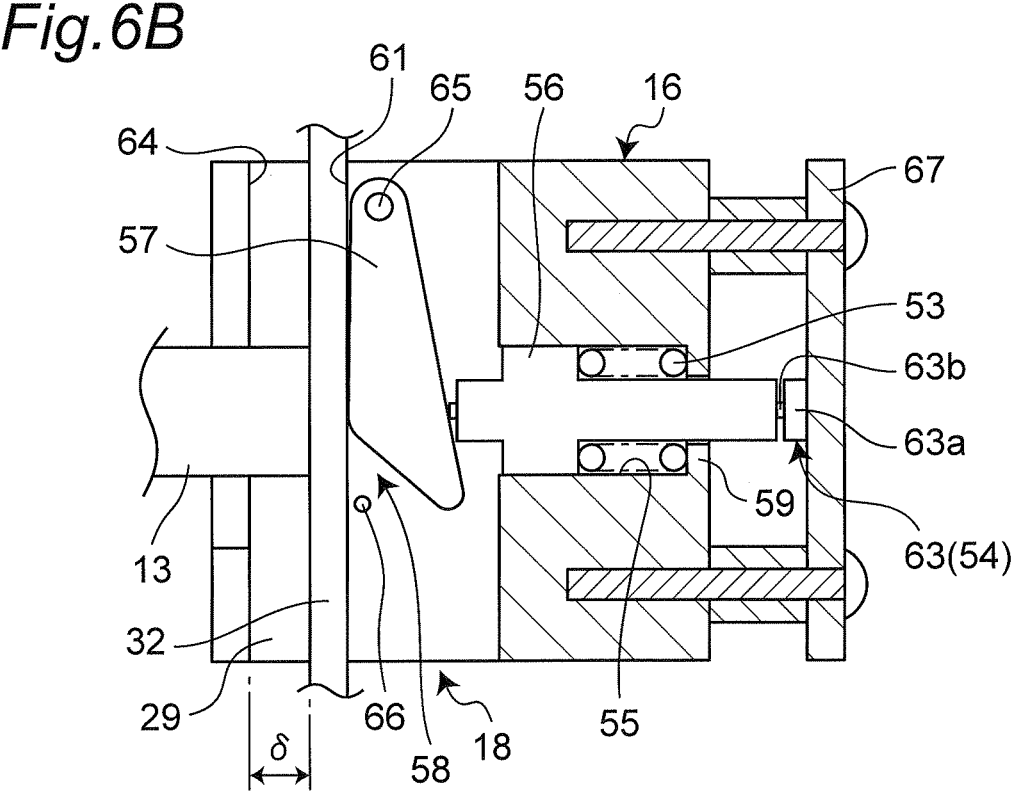
FIG. 6B is a sectional pattern view of the holder according to the first embodiment in the state where the press section and the push surface are in contact with each other.
Figure 6C:
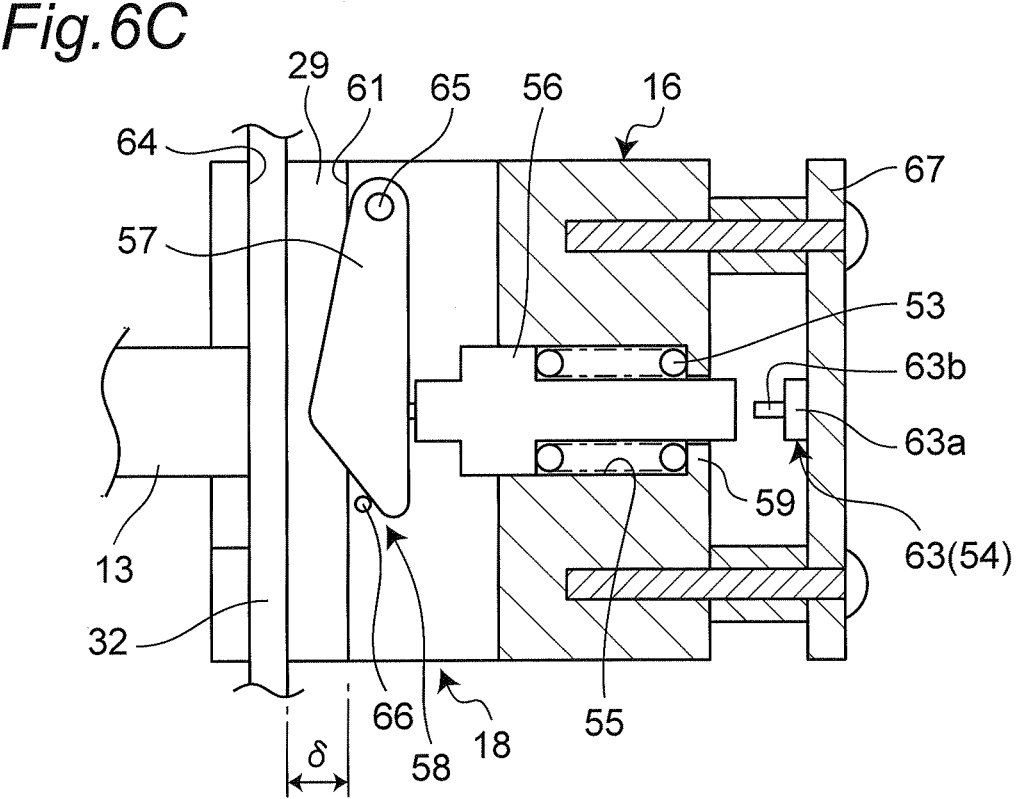
FIG. 6C is a sectional pattern view of the holder according to the first embodiment in a state where the press section and a front surface are in contact with each other.

With reference to FIGS. 6A to 6E, the holder 16 is provided, in the front portion, with the recess 29, front and rear ends of which are defined by a front surface 64 and a push surface 61, respectively. The press section 32 of the plunger 13 is accommodated in this recess 29. The recess 29 has a width (the distance between the front surface 64 and the push surface 61) that is set to be larger than the thickness of the press section 32. As shown in FIG. 6B, when the plunger 13 is moved forward so as to be pushed toward the outer tube 14, the push surface 61 of the holder 16 is brought into contact with the press section 32. On the other hand, as shown in FIG. 6C, when the plunger 13 is moved backward so as to be pulled out of the outer tube 14, the front surface 64 of the holder 16 is brought into contact with the press section 32.

The internal pressure detector 18 includes a movable section 58 that is in contact with a bottom surface of the press section 32 of the plunger 13, a bias spring 53 serving as an elastically biasing portion that elastically presses the movable section 58 toward the plunger 13, and the positive pressure detection switch 63 that is operated by the movable section 58 in accordance with the internal pressure of the syringe 12 so as to be turned ON or OFF.

The movable section 58 has a free piece 56 that is supported by a cylindrical section 55 having respectively open ends and provided at the holder 16 and can reciprocate along the axis of the plunger 13, and a swing piece 57 that is located adjacent to the push surface 61 of the holder 16 and has an upper end rotatably supported at a support 65. The bias spring 53 is held between the free piece 56 and a brim section 59 of the cylindrical section 55, and applies a force for pressing the free piece 56 toward the plunger 13. There is provided a stopper 66 that is located adjacent to a lower end of the swing piece 57 and restricts rotation of the swing piece 57 against the bias force of the bias spring 53. The free piece 56 has another end (right end in the figures) which projects backward from the cylindrical section 55. The positive pressure detection switch 63 is fixed to an attachment member 67 that is secured at a position spaced apart from the rear portion of the holder 16, and faces the other end of the free piece 56.

Figure 6D:
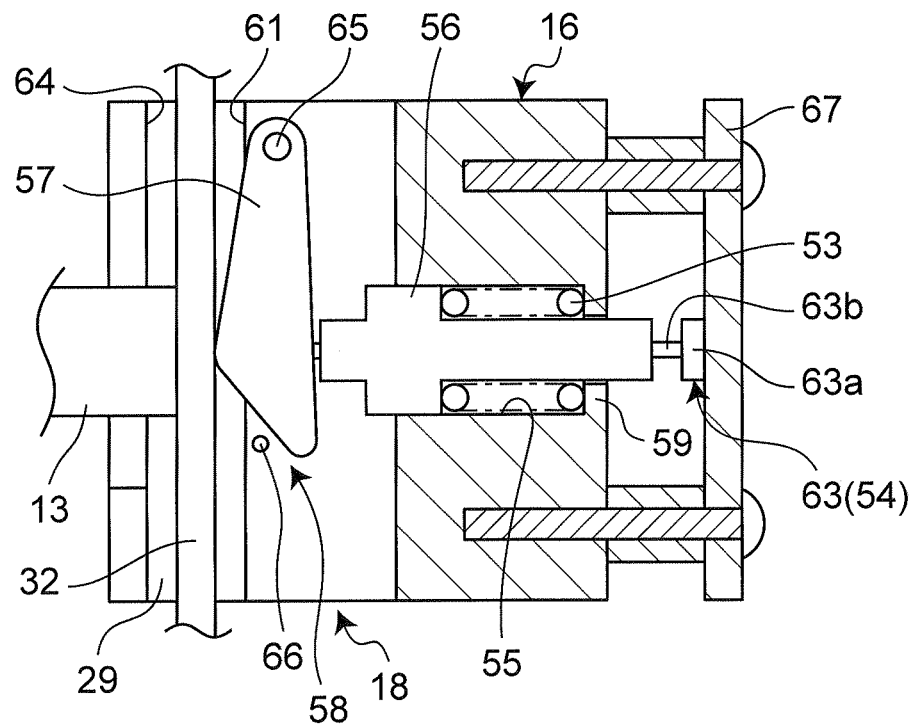
FIG. 6D is a sectional pattern view of the holder according to the first embodiment in a state where the press section is located apart from the push surface and the front surface (in a case of a positive pressure).
Figure 6E:
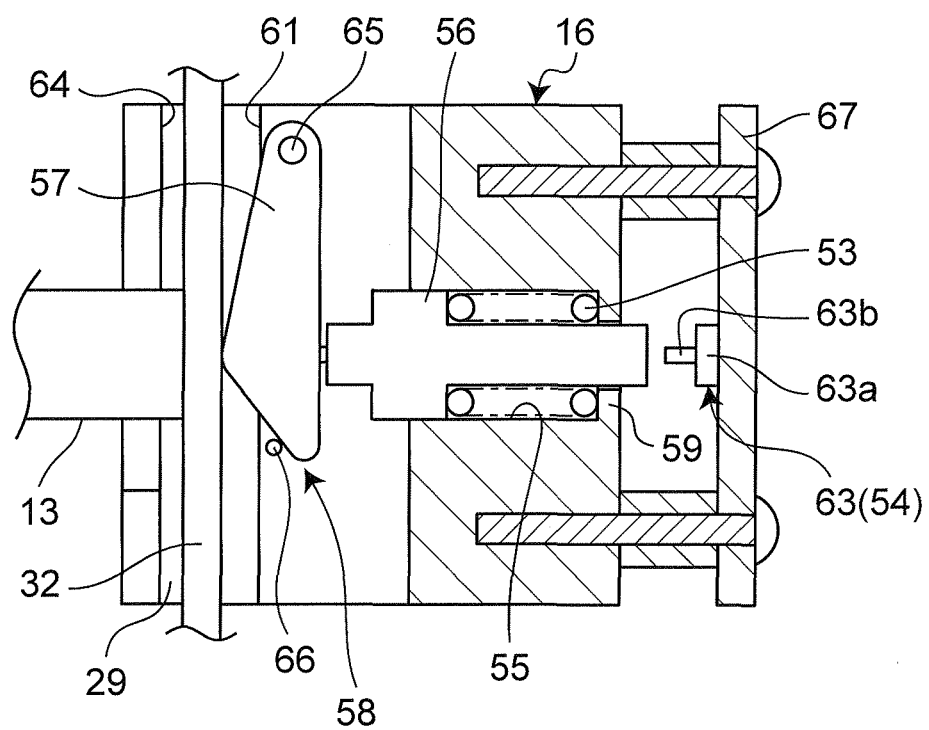
FIG. 6E is a sectional pattern view of the holder according to the first embodiment in the state where the press section is located apart from the push surface and the front surface (in a case of a negative pressure).

The positive pressure detection switch 63 takes the two states, namely, the ON state (such as shown in FIGS. 6B and 6D) and the OFF state (such as shown in FIGS. 6C and 6E). In the ON state, an operation piece 63b is pushed into a main body 63a by a distance not less than a certain degree. In the OFF state, the operation piece 63b is not pushed into the main body 63a or is pushed thereinto by a distance less than the certain degree. The positive pressure detection switch 63 is set to be ON in a case where a force applied from the free piece 56 to the operation piece 63b pulling the plunger 13 is not less than a value corresponding to the alert value of the internal pressure of the syringe 12, due to the characteristics such as resistance to be applied when the operation piece 63b is pushed into the main body 63a. Therefore, the positive pressure detection switch 63 being in the ON state indicates that the internal pressure of the syringe 12 is not less than the alert value. To the contrary, the positive pressure detection switch 63 being in the OFF state indicates that the internal pressure of the syringe 12 is less than the alert value. The result regarding whether the positive pressure detection switch 63 is ON or OFF, in other words, whether the internal pressure of the syringe 12 detected by the internal pressure detector 18 is not less than or is less than the alert value, is outputted to the determination section 41.

Figure 5A:
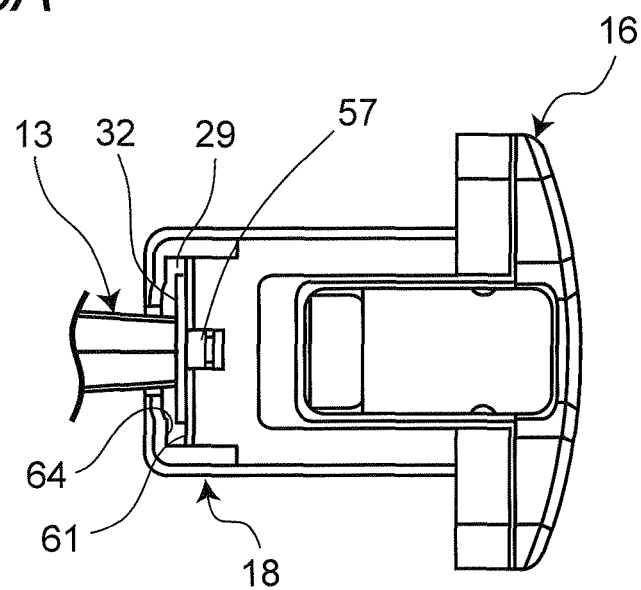
FIG. 5A is a top view of the holder according to the first embodiment in a state where a press section and a push surface are in contact with each other.

FIGS. 5A and 6B each show a state where the holder 16 pushes the plunger 13. Viscous resistance of the medicinal solution is applied while the holder 16 is pushing the plunger 13. Accordingly, the force for pushing the plunger 13 by means of the holder 16 is much larger than the force of the bias spring 53 pressing the swing piece 57. Therefore, the swing piece 57 is pushed against the force of the bias spring 53, and the press section 32 of the plunger 13 and the push surface 61 of the holder 16 are brought into contact with each other. Because the swing piece 57 is pushed in this manner, the operation piece 63b of the positive pressure detection switch 63 is pushed into the main body 63a by the free piece 56 by a distance not less than the certain degree, with a result that the positive pressure detection switch 63 is turned ON. In this case, the force for pushing the plunger 13 by means of the holder 16 is quite large, such as more than one hundred N in some cases. The force applied to the plunger 13 is transmitted to the positive pressure detection switch 63 by way of the swing piece 57 in this manner. The positive pressure detection switch 63 can be prevented from being damaged by such an excessive load of more than one hundred N if the push surface 61 is configured to receive the force of such an excessive load.

FIG. 6C shows a state where the holder 16 pulls the plunger 13. While the holder 16 is pulling the plunger 13, the press section 32 of the plunger 13 is in contact with the front surface 64, and is not in contact with the swing piece 57. Accordingly, while the holder 16 is pulling the plunger 13, no force is applied from the plunger 13 to the operation piece 63b of the positive pressure detection switch 63 by way of the swing piece 57 and the free piece 56, whereby the positive pressure detection switch 63 is OFF.

Figure 5B:
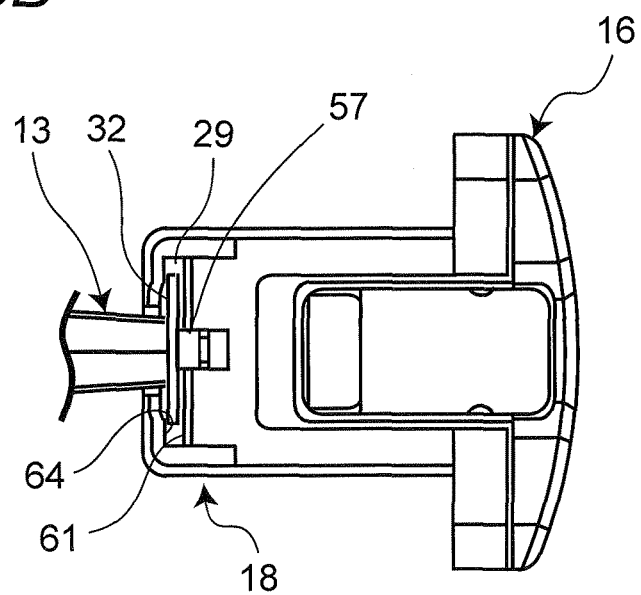
FIG. 5B is a top view of the holder according to the first embodiment 1 in a state where the press section and the push surface are located apart from each other.

FIGS. 5B, 6D, and 6E each show a state where the press section 32 of the plunger 13 and the push surface 61 of the holder 16 are spaced apart from each other upon detection of the internal pressure of the syringe 12 while the holder 16 is stopped. In this state, the internal pressure of the syringe 12 is applied as a force for pressing the positive pressure detection switch 63 so as to pull the plunger 13, by way of the press section 32 of the plunger 13 and the swing piece 57. The positive pressure detection switch 63 is turned ON (FIG. 6D) or is turned OFF (FIG. 6E) depending on the magnitude of this force (whether or not to correspond to the pressure not less than the alert value as described above). If the internal pressure of the syringe 12 is much larger than the alert value even upon detection of the internal pressure of the syringe 12 while the holder 16 is stopped, the plunger 13 is located such that the press section 32 is in contact with the push surface 61, as shown in FIG. 6B. If the syringe 12 has a negative internal pressure even upon detection of the internal pressure of the syringe 12 while the holder 16 is stopped, the plunger 13 is located such that the press section 32 is in contact with the front surface 64.

The bias spring 53 biases the press section 32 of the plunger 13 so as to push the plunger 13 by way of the movable section 58 (the free piece 56 and the swing piece 57). The force of the bias spring 53 biasing the plunger 13 is set not to be less than the syringe frictional force mentioned earlier. The reason therefor is stated below.

A force of about 4 N, which may be generated as the frictional force between the gasket 62 of the plunger 13 and the outer tube 14, can be converted in accordance with the area of the gasket to a pressure of about 5 kPa. Thus, if the internal pressure of the syringe is detected under a condition where the bias spring 53 is not provided, even in a case where the internal pressure of the syringe 12 reaches a level at which medicinal solution aerosolization possibly occurs, that is, the alert value, the force of the internal pressure of the syringe 12 pushing the plunger 13 is less than the frictional force between the gasket 62 and the outer tube 14 (the syringe frictional force). Therefore, the plunger 13 is not moved so as to be pulled and the positive pressure detection switch 63 is kept OFF. In this case, a force sensor 54 cannot accurately detect the internal pressure of the syringe 12 even though medicinal solution aerosolization may possibly occur, with a result that the operator cannot be precisely alerted in accordance with determination made by the determination section 41. To the contrary, in the present embodiment, the force of the bias spring 53 biasing the press section 32 of the plunger 13 is set not to be less than the syringe frictional force. Therefore, even in a case where the internal pressure of the syringe 12 is less than the syringe frictional force, the internal pressure of the syringe 12 can be detected with a high degree of accuracy as the ON/OFF state of the positive pressure detection switch 63.

More specifically, the force of the bias spring 53 biasing the plunger 13 by way of the movable section 58 is set not to be less than a static frictional force between the gasket 62 of the plunger 13 and the outer tube 14. If the bias force of the bias spring 53 is set to be too large, accuracy in detection of the internal pressure of the syringe 12 in accordance with the ON/OFF state of the positive pressure detection switch 63 is degraded. It is thus preferred to set the bias force of the bias spring 53 so as to be slightly larger than the static frictional force between the gasket 62 and the outer tube 14.

Figure 7A:
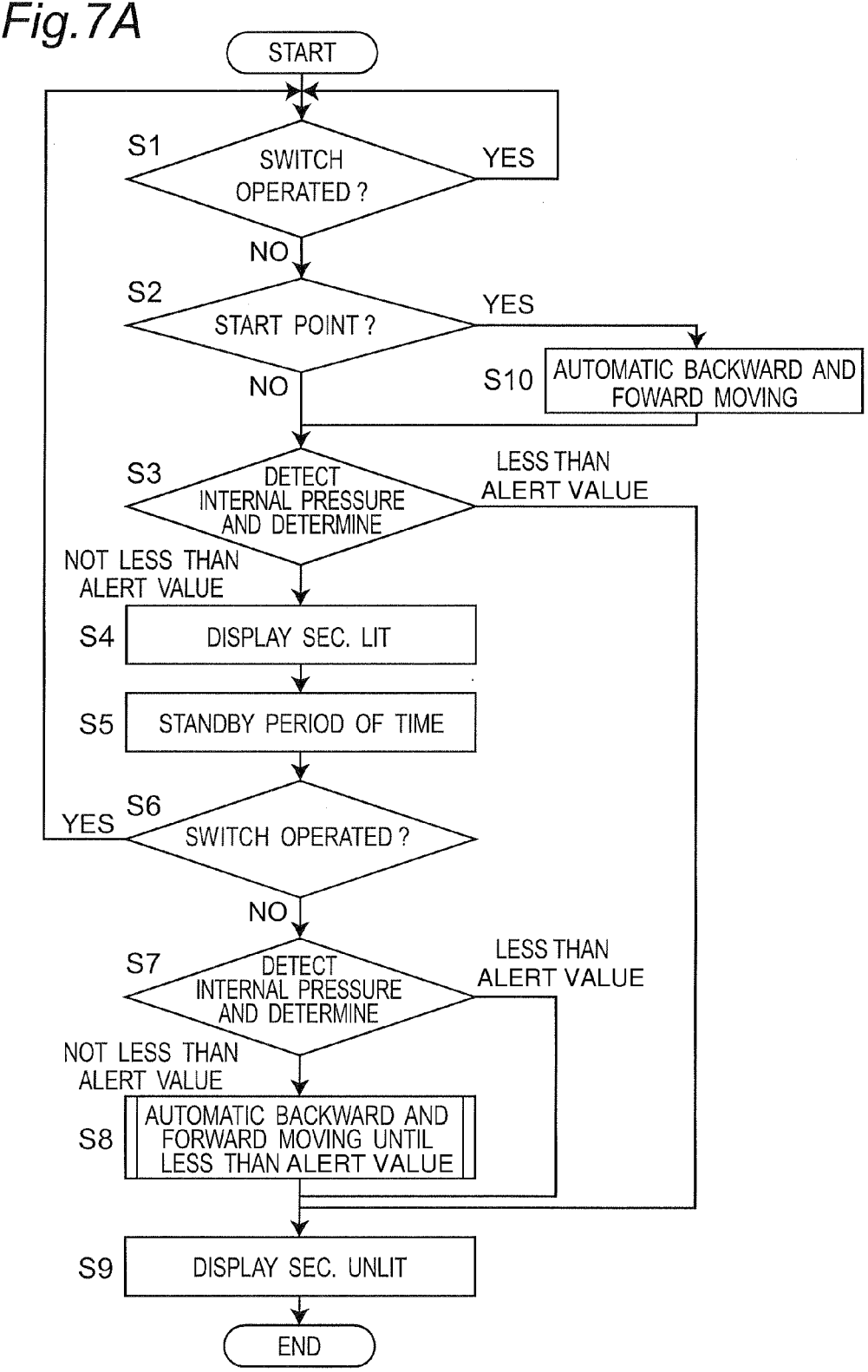
FIG. 7A is a flowchart of the operation steps in an automatic mode of the syringe drive device according to the first embodiment.

Described next are the operation steps of the syringe drive device 11 according to the present embodiment with reference to the flowchart in FIG. 7A. In FIG. 7A, the mode switch 49 (FIG. 3) is ON, in which case the automatic mode is effected. Unless otherwise specified, processing in each of the steps in FIG. 7A is executed by the determination section 41.

Initially in step S1, it is checked whether or not the operation switch 17 is operated so as to be in a position other than the neutral position, in other words, the pull command is ON or the push command is ON. If the operation switch 17 is not operated such that the pull command or the push command is ON in step S1, that is, if the operation switch 17 is in the neutral position, the process goes to step S2. In this case, the operator does not perform the aspiration operation or the discharge operation, and the holder 16 moving the syringe 12 is stopped.

In step S2, it is determined whether or not the start point detection sensor 47 is ON. If the start point detection sensor 47 is OFF, the process goes to step S3 and the result of determination is checked with regard to detection of the internal pressure. As described earlier, the determination section 41 according to the present embodiment constantly determines whether or not the internal pressure of the syringe 12 detected by the internal pressure detector 18 is not less than the alert value, more specifically, whether the positive pressure detection switch 63 is ON or OFF.

Figure 8A:
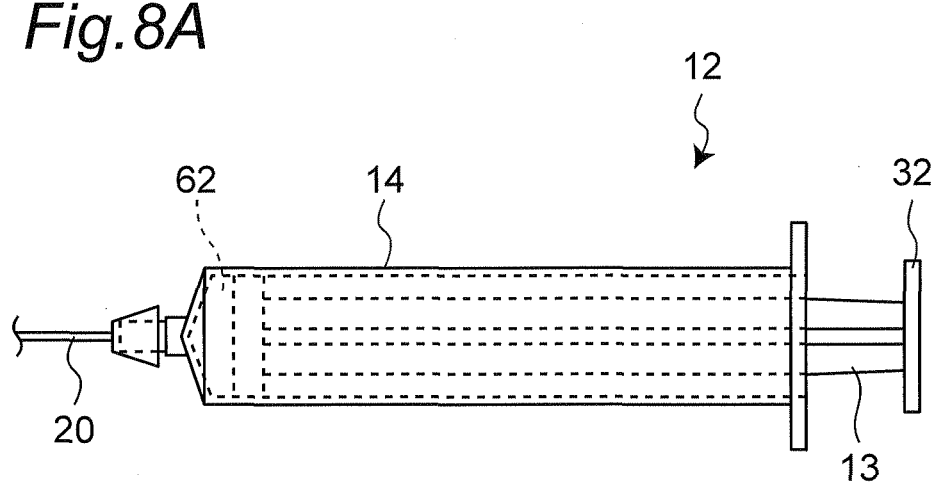
FIG. 8A is a plan view of a syringe in a state where a plunger is located at a start point.
Figure 8B:
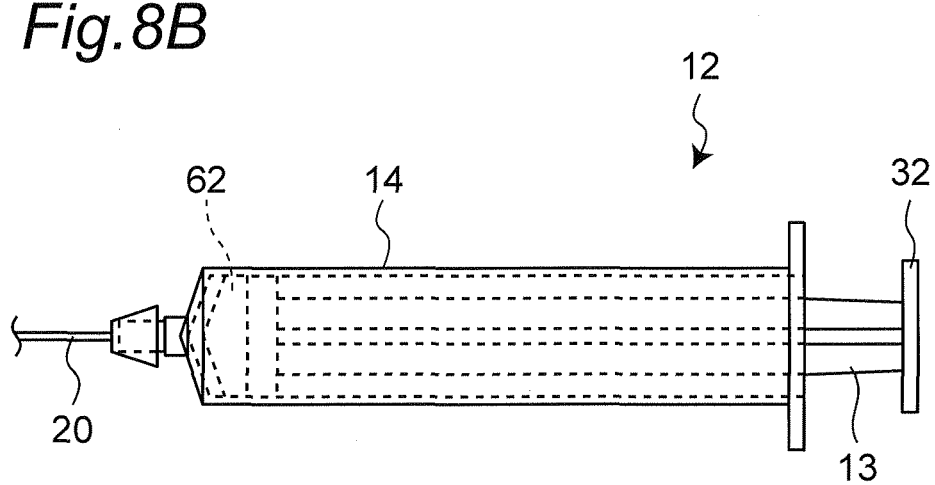
FIG. 8B is a plan view of the syringe in a state where the plunger is located behind the start point.
Figure 9:
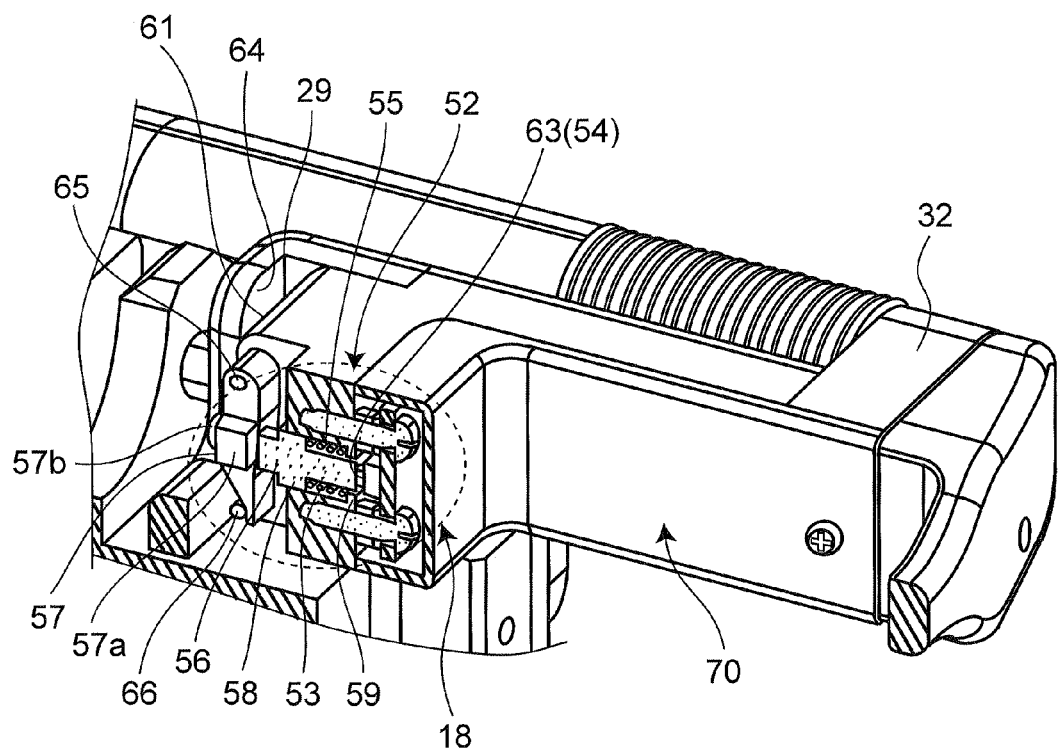
FIG. 9 is a perspective view of a holder according to a second embodiment of the present invention, in which the holder is partially shown in cross section.

On the other hand, if the start point detection sensor 47 is ON, the process goes to step S10, where the following processing is performed. If the start point detection sensor 47 is ON, as shown in FIG. 8A, the plunger 13 is pushed toward the outer tube 14 such that the gasket 62 reaches the distal end of the outer tube 14. Further, when the start point detection sensor 47 is ON, as shown in FIG. 6B, the press section 32 of the plunger 13 is pressed against the push surface 61. It is thus impossible to detect the internal pressure of the syringe 12 in accordance with the force applied from the movable section 58 to the positive pressure detection switch 63. Accordingly, in step S10, the drive section 42 initially moves the holder 16 so that the gasket 62 is moved from the position at the distal end of the outer tube 14 as shown in FIG. 8A to a position spaced apart from the distal end of the outer tube 14 as shown in FIG. 8B. In this manner, the plunger 13 is moved backward so as to be pulled by a predetermined distance. After the plunger 13 is moved backward, as shown in FIG. 6C, the press section 32 of the plunger 13 is in contact with the front surface 64.

In Step S10, the drive section 42 subsequently moves the holder 16 so as to push the plunger 13 by a slight distance δ (FIGS. 6B and 6C) corresponding to a difference obtained by subtracting the thickness of the press section 32 of the plunger 13 from the distance between the push surface 61 and the front surface 64. This forward movement brings the press section 32 of the plunger 13 into the state where its movement is not restricted either by the push surface 61 or by the front surface 64. As a result, the plunger 13 is moved in the direction and by the distance, each of which corresponds to the internal pressure of the syringe 12. In more detail, if the syringe 12 has a positive internal pressure, the plunger 13 moves so as to be pulled. On the other hand, if the syringe 12 has a negative internal pressure, the plunger 13 is moved so as to be pushed. As a result, the internal pressure of the syringe 12 can be detected by means of the positive pressure detection switch 63. More specifically, after the forward movement by the distance δ, the positive pressure detection switch 63 is turned ON (FIG. 6D or 6B) or is turned OFF (FIG. 6E or 6C) depending on whether the internal pressure of the syringe 12 is not less than the alert value or is less than the alert value, as described earlier. The distance δ is preferably from about 0.5 mm to 1 mm. The distance δ set not to be less than 0.5 mm facilitates attaching and detaching the syringe 12. If the distance δ is too large such as exceeding 1 mm, the swing piece 57 or the like needs to be moved by a longer distance, with an unpreferred result that the structure is increased in size. The distance of the backward movement is preferably from about 1 mm to 2 mm in most cases, while being varied depending on the distance δ. When the distance of the backward movement is set not to be less than 1 mm, the front surface 64 is brought into contact with the press section 32 of the plunger 13, which is therefore reliably moved backward. If the distance of the backward movement is too large such as exceeding 2 mm, unnecessary aspiration may be possibly performed, which is not preferred.

Because the plunger 13 is automatically moved backward in step S10, the syringe 12 is not rigidly held between the fixing section 15 and the holder 16 even in a case where the plunger 13 is pushed to reach the start point of the syringe. Therefore, no excessive load is applied to the syringe drive device 11 or to the syringe 12, thereby assuring safety.

Checked in step S3 is the result of detection of the internal pressure of the syringe 12 and determination, that is, whether the internal pressure of the syringe 12 is not less than the alert value (the positive pressure detection switch 63 is ON) or is less than the alert value (the positive pressure detection switch 63 is OFF). The force applied from the press section 32 of the plunger 13, which corresponds to the internal pressure of the syringe 12, is transmitted to the positive pressure detection switch 63 by way of the movable section 58. The free piece 56 of the movable section 58 biases the plunger 13 so as to be pushed using the bias force of the bias spring 53 which is not less than the static frictional force between the gasket 62 and the outer tube 14. It is thus possible to eliminate or reduce the influence of the static frictional force, and the internal pressure of the syringe 12 can be detected with a high degree of accuracy as the ON/OFF state of the positive pressure detection switch 63. Therefore, possibility of occurrence of medicinal solution aerosolization can be determined accurately.

If the detection value of the internal pressure of the syringe 12 is less than the alert value in step S3, the red LED 36 in the display section 19 is unlit in step S9, as the end of the process. On the other hand, if the detection value of the internal pressure of the syringe 12 is not less than the alert value in step S3, the red LED 36 is lit in step S4. Then, after a predetermined standby period of time elapses in step S5, the process goes to step S6. In step S6, similarly to step S1, it is checked again whether or not the operation switch 17 is in the neutral position (neither the pull command nor the push command is ON). If the operation switch 17 is in the neutral position (the operator performs neither the aspiration operation nor the discharge operation, and the holder 16 moving the syringe 12 is stopped) in step S6, the process goes to step S7. The standby period of time is preferably set to about one second. In order to reliably detect that the operator is performing neither the aspiration operation nor the discharge operation, it is not preferred to set the standby period of time to be too short.

Checked again in step S7 is the result of detection of the internal pressure of the syringe 12 and determination, that is, whether or not the internal pressure of the syringe 12 detected as the ON/OFF state of the positive pressure detection switch 63 is not less than the alert value. If the detection value of the internal pressure of the syringe 12 is less than the alert value in step S7, the red LED 36 in the display section 19 is unlit in step S9, as the end of the process. On the other hand, if the detection value of the internal pressure of the syringe 12 is not less than the alert value in step S7, the process goes to step S8.

In step S8, the holder 16 of the plunger 13 repetitively moves forward and backward until the internal pressure of the syringe 12 is detected to be not more than the alert value (the positive pressure detection switch 63 is turned OFF).

Step S8 is detailed with reference to FIG. 7C. Initially in step S101, the drive section 42 moves the holder 16 so as to pull the plunger 13 by a predetermined distance of backward movement, and the plunger 13 is thus moved so as to be pulled. The distance of the backward movement of the holder 16 can be determined in accordance with the size of the syringe 12, viscosity of the medicinal solution in the syringe 12, and the like. As shown in FIG. 6C, after this backward movement, the press section 32 of the plunger 13 is in contact with the front surface 64. Subsequently in step S102, the drive section 42 moves the holder 16 so as to push the plunger 13 by the slight distance δ (FIGS. 6B and 6C) corresponding to the difference obtained by subtracting the thickness of the press section 32 of the plunger 13 from the distance between the push surface 61 and the front surface 64. The distance of the backward movement is preferably from about 1 mm to 2 mm in most cases, while being varied depending on the distance of movement to push the plunger. When the distance of the backward movement is set not to be less than 1 mm, the front surface 64 is brought into contact with the press section 32 of the plunger 13, which is therefore reliably moved backward. If the distance of the backward movement is too large such as exceeding 2 mm, unnecessary aspiration may be possibly performed, which is not preferred. The distance of the backward movement of the holder 16 in step S101 needs to be set to be larger than the distance δ. The forward movement in step S102 brings the press section 32 of the plunger 13 into the state where its movement is not restricted either by the push surface 61 or by the front surface 64. As a result, the plunger 13 is moved in the direction and by the distance, each of which corresponds to the internal pressure of the syringe 12. The process further goes to step S103, in which the result of determination is checked with regard to whether the internal pressure of the syringe 12 is not less than the alert value (the positive pressure detection switch 63 is ON) or is less than the alert value (the positive pressure detection switch 63 is OFF). If the internal pressure of the syringe 12 is not less than the alert value in step S103, the processing in step S101 (backward movement of the holder 16) and the processing in step S102 (forward movement of the holder 16) are executed repetitively. If the internal pressure of the syringe 12 is less than the alert value in step S103, the process goes to step S9 in FIG. 7A. Because the plunger 13 is automatically moved forward and backward in this manner until the positive pressure detection switch 63 is turned OFF, the internal pressure of the syringe 12 can be reduced to a level where medicinal solution aerosolization does not occur.

Figure 7B:
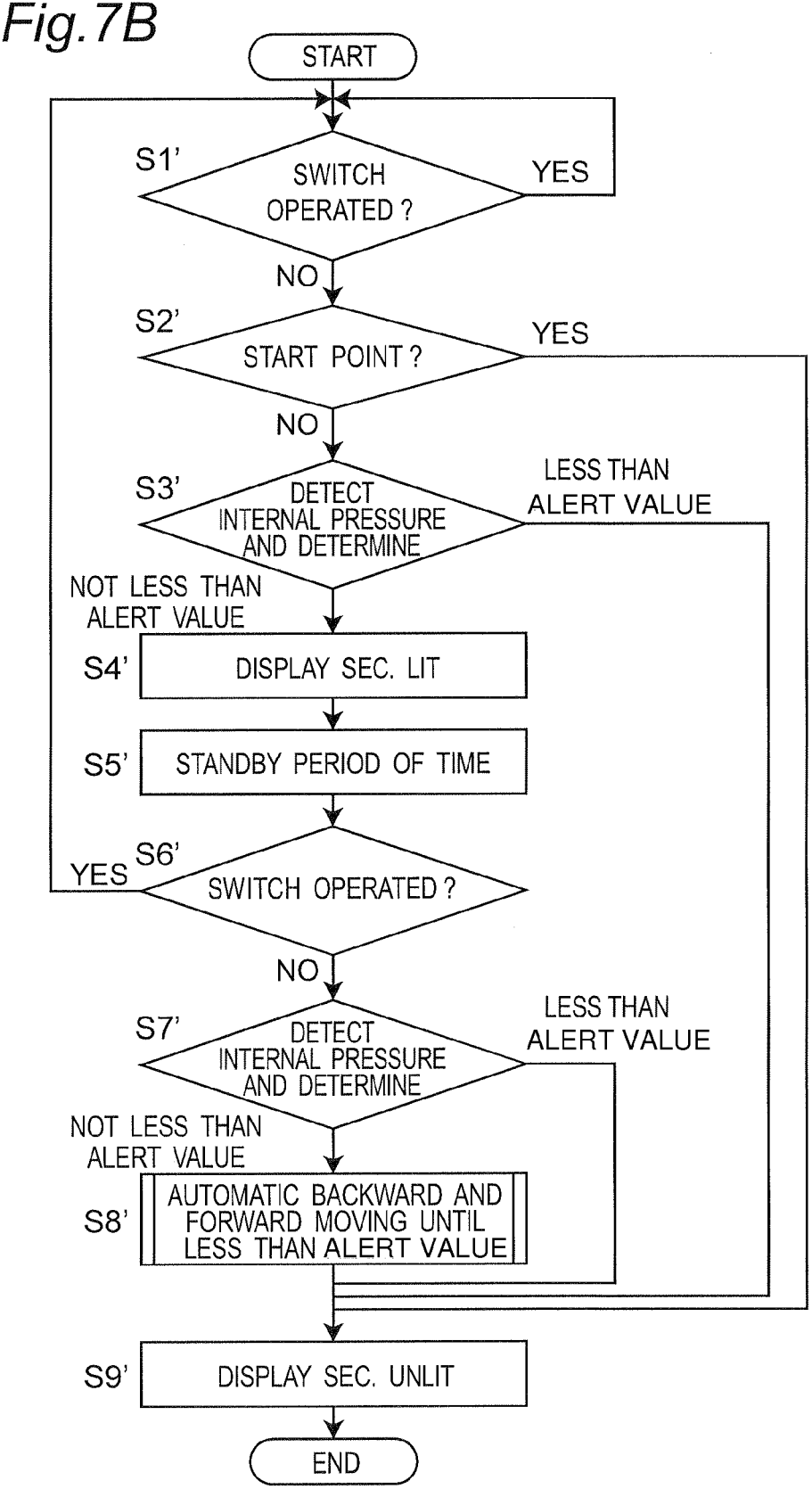
FIG. 7B is a flowchart of an alternative example of the operation steps in the automatic mode of the syringe drive device according to the first embodiment.
Figure 7C:
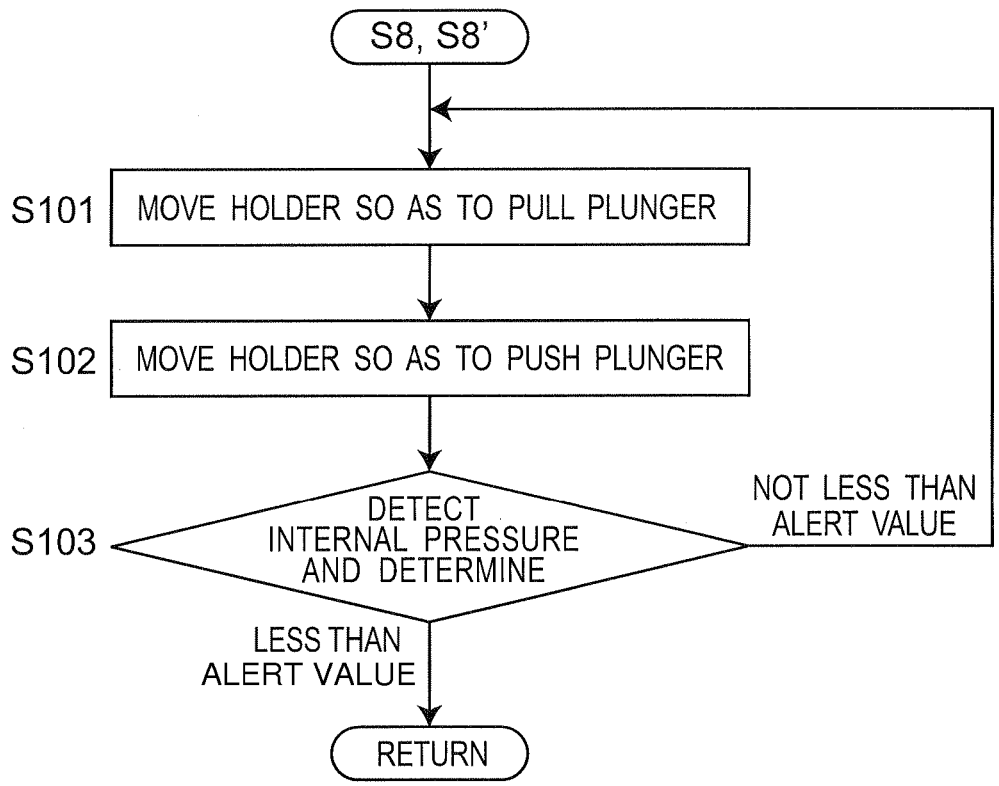
FIG. 7C is a flowchart showing details of step S8 in FIG. 7A and step S8' in FIG. 7B.

FIG. 7B shows another automatic mode as an alternative example of the automatic mode shown in FIG. 7A. Steps S1' to S9' in this alternative example are similar to those shown in FIG. 7A, while the plunger 13 is not automatically moved backward or forward (step S10 in FIG. 7A) when the start point detection sensor 47 is ON. In this alternative example, if it is detected that the start point detection sensor 47 is ON in step S2', the LED 36 is unlit in step S9', as the end of the process. More specifically, in this alternative example, in the case where the holder 16 pushes the plunger 13 so as to reach the start point of the syringe, no alert is issued as to the occurrence of medicinal solution aerosolization. This is because, as is quite obvious to any operator experienced in mixing medicinal solutions, that when the plunger 13 is pushed to reach the start point of the syringe, the internal pressures of the syringe 12 and the vial are not at the level where medicinal solution aerosolization occurs. In such a configuration, an alert to the occurrence of medicinal solution aerosolization can be issued under the conditions desired by such an experienced operator.

FIG. 7D shows the operation steps of the syringe drive device 11 according to the present embodiment in the case where the mode switch 49 (FIG. 3) is OFF, namely, in a non-automatic mode. In the automatic mode (where the mode switch 49 is ON) described with reference to FIG. 7A, if the internal pressure of the syringe 12 is once determined to be not less than the alert value (the positive pressure detection switch 63 is ON), determination is performed again after the standby period of time elapses with regard to whether or not the internal pressure of the syringe 12 is not less than the alert value, as described earlier. If the internal pressure of the syringe 12 is not less than the alert value, the holder 16 is repetitively moved forward and backward until the internal pressure is reduced to be less than the alert value (steps S5 to S8 in FIG. 7A, as well as FIG. 7C). These operation steps are not executed in the non-automatic mode shown in FIG. 7D. The other operation steps in the non-automatic mode shown in FIG. 7D, namely, steps S201 to S204, S209, and S210, are the same as steps S1 to S4, S9, and S10 in the automatic mode shown in FIG. 7A, respectively. FIG. 7E shows another non-automatic mode as an alternative example. FIG. 7E is different from FIG. 7D in that, in the case where the start point detection sensor 47 is ON in step S210', the holder 16 is not automatically moved backward or forward. The other operation steps in FIG. 7E, namely, steps S201' to S204' and S209', are the same as steps S201 to S204 and S209 in FIG. 7D, respectively.

In the syringe drive device 11 according to the present embodiment, the positive pressure detection switch 63 may be replaced with the force sensor 54, which is configured as a piezoelectric element sensor or the like. The force sensor 54 detects a force transmitted through the free piece 56 of the movable section 58, that is, the force for pressing, by way of the swing piece 57, the free piece 56 so as to pull the plunger 13 by means of the bottom surface of the press section 32 of the plunger 13, and outputs the result of detection to the determination section 41. The determination section 41 converts the detection value received from the force sensor 54 into the internal pressure of the syringe 12, and compares the converted internal pressure with the alert value, which is preliminarily stored. As described earlier, detection of the internal pressure and determination are performed in steps S3 and S7 in FIG. 7A, steps S3' and ST in FIG. 7B, step S103 in FIG. 7C, step S203 in FIG. 7D, and step S203' in FIG. 7E. In the case where the force sensor 54 is adopted, such detection of the internal pressure and determination are executed as a comparison between the alert value and the internal pressure converted from the detection value of the force sensor 54.

In the case where the positive pressure detection switch 63 is replaced with the force sensor 54, the determination section 41 can calculate or estimate an appropriate distance of backward movement in accordance with the detection value of the force sensor 54 when the holder 16 (plunger 13) is automatically moved backward upon detection of the start point (step S10 in FIG. 7A or step S210 in FIG. 7D). Further, in this case, the determination section 41 can calculate or estimate an appropriate distance of backward movement in accordance with the detection value of the force sensor 54 when the holder 16 (plunger 13) is automatically moved backward upon detection of a positive pressure in the automatic mode (step S8 in FIG. 7A and step S8' in FIG. 7B). For example, if the force sensor 54 has a large detection value, the distance of the backward movement is set to be large. In particular, by calculating the distance of automatic backward movement of the holder 16 (plunger 13) in accordance with the detection value of the force sensor 54 upon detection of a positive pressure in the automatic mode, the number of times of repetitive forward and backward movement (FIG. 7C) of the holder 16 can be reduced considerably.

The determination section 41 calculates the internal pressure in accordance with the following expression, for example.

Internal pressure [Pa]={Detection value of force sensor [*N*]+(Bias force of bias spring [*N*])−Kinetic frictional force [*N*])}/Area of syringe [m2] [Expression 1]

The determination section 41 may perform determination after the drive section pushes the holder 16 toward the plunger 13 and stops and then a period of time elapses during which the bias spring is restored. Immediately after the holder 16 pushes the plunger 13 and stops, the press section 32 and the push surface 61 are in contact with each other in most cases. Even in a case where the internal pressure of the syringe 12 is less than the threshold for the movement, it takes time for the plunger 13 to be pushed by the bias spring 53, though being very short. Accordingly, after elapse of the period of time for restoration of the bias spring, during which the bias spring 53 returns to the original state, it may be determined whether or not to issue an alert. This case realizes more accurate issue of an alert to occurrence of medicinal solution aerosolization. The period of time for restoration of the bias spring is determined depending on the bias force of the bias spring, stroke of the operation piece 63*b* of the positive pressure detection switch, the frictional force, and the like. Determination may be performed after about 100 ms, for example.

Second Embodiment

A syringe drive device 11 shown in FIGS. 9 to 12 according to a second embodiment is different from that of the first embodiment, in that it is possible to adjust the force for pressing the plunger 13 so as to be pushed by means of the movable section 58 of the internal pressure detector 18 using the bias force of the bias spring 53.

The syringe frictional force is varied in accordance with the size of the gasket 62, in other words, the content of the syringe to be used. The force for pushing the plunger 13 by means of the movable section 58 using the bias spring 53 is adjustable in correspondence with the syringe 12 to be used. Therefore, even though the syringe has a different content, it is possible to appropriately eliminate or reduce the influence of the frictional force and calculate the internal pressure of the syringe 12 with a high degree of accuracy in accordance with the state of the positive pressure detection switch 63 or the detection value of the force sensor 54. As a result, an alert can be issued accurately to occurrence of medicinal solution aerosolization.

In the second embodiment, the holder 16 according to the first embodiment is replaced with a holder 70, which is thus particularly described.

Figure 10:
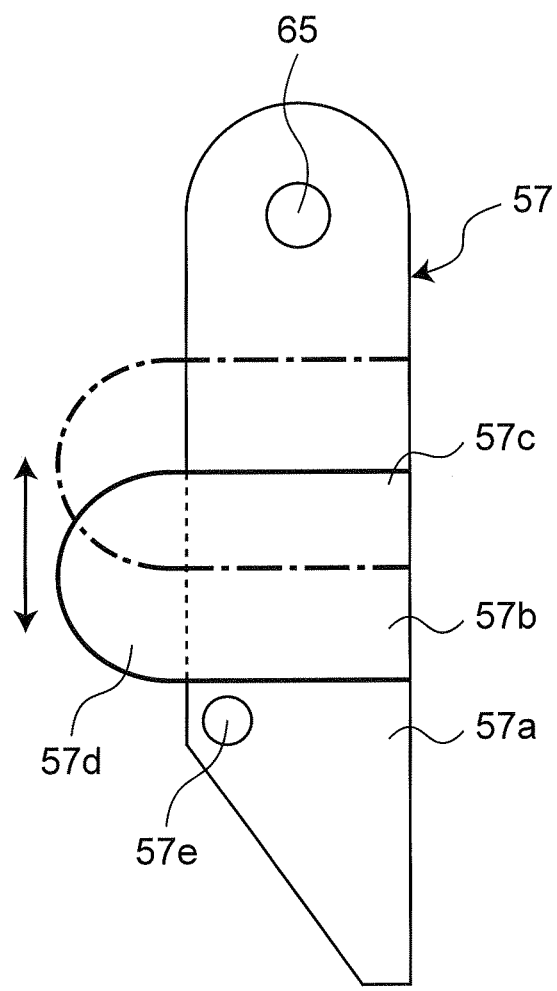
FIG. 10 is a side pattern view of a swing portion according to the second embodiment of the present invention.
Figure 11:
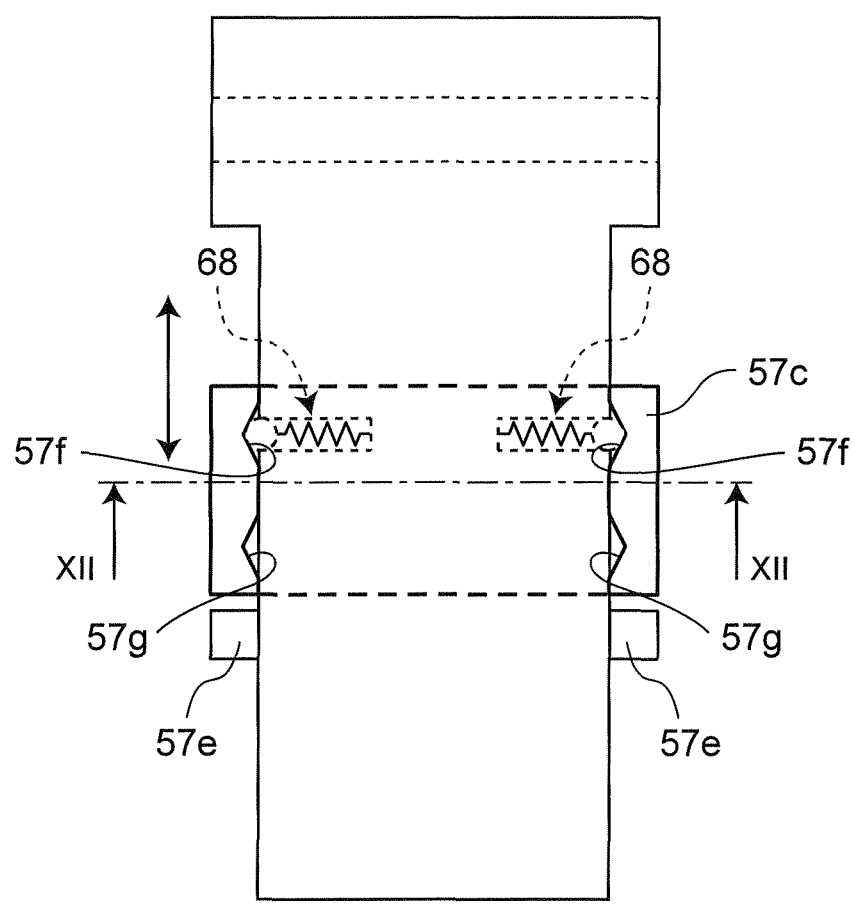
FIG. 11 is a rear pattern view of the swing portion according to the second embodiment of the present invention.
Figure 12:
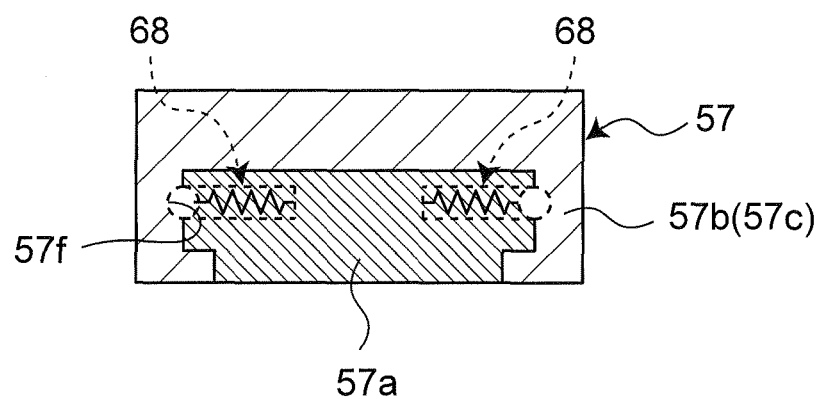
FIG. 12 is a sectional view taken along line XII-XII indicated in FIG. 11.

The swing piece 57 has a main body 57a and a projection 57b that is slidable upward and downward on the main body 57a and can be positioned thereon. The projection 57b has a base portion 57c that is guided by the main body 57a, and a contact portion 57d that projects from the base portion 57c and is in contact with the press section 32 of the plunger 13. The main body 57a is provided with a catcher 57e that prevents disengagement of the projection 57b through a lower end. The projection 57b is provided, inside the base portion 57c, with paired grooves 57f and paired grooves 57g, which are located at two levels of an upper level and a lower level, respectively. Further, the main body 57a is provided with paired ball plungers 68. When balls of the ball plungers 68 are engaged with the grooves 57g out of the grooves provided at the two levels of the upper and lower levels, the projection 57b can be set with respect to the main body 57a at an upper position as indicated by a dashed line in FIG. 10. On the other hand, when the balls are engaged with the grooves 57f, the projection 57b can be set with respect to the main body 57a at a lower position as indicated by a solid line in FIG. 10.

In such a configuration, the force for pushing the plunger 13 by means of a modified swing piece 71 is adjusted by sliding a convex portion 72 upward or downward. The swing piece 57 rotates about the support 65 that is located above the projection 57b. When the projection 57b is set at the lower position (the grooves 57g), in comparison to the case where the projection 57b is set at the upper position (the grooves 57f), the distance between the free piece 56 serving as a power point and the support 65 is not changed, but a point of action of the force applied to the plunger 13 is located farther. Therefore, it is possible to reduce the force for pushing the plunger 13 by means of the swing piece 57 without changing the spring force of the bias spring 53. To the contrary, when the projection 57b is set at the upper position (the grooves 57f), in comparison to the case where the projection 57b is set at the lower position (the grooves 57g), the distance between the free piece 56 serving as the power point and the support 65 is not changed, but the point of action of the force applied to the plunger 13 is located closer. Therefore, it is possible to increase the force for pushing the plunger by means of the swing piece 57 without changing the spring force of the bias spring 53.

Further, when the projection 57b serving as a contact point is located at the lower position for the syringe 12 having a small diameter, it is possible to apply the force to the center and the vicinity thereof on the bottom surface of the press section 32. On the other hand, when the projection 57b is located at the upper position for the syringe 12 having a large diameter, it is possible to apply the force to the center and the vicinity thereof on the bottom surface of the press section 32. In summary, the force can be efficiently transmitted to the plunger 13 for the syringe 12 having a different content.

Figure 7D:
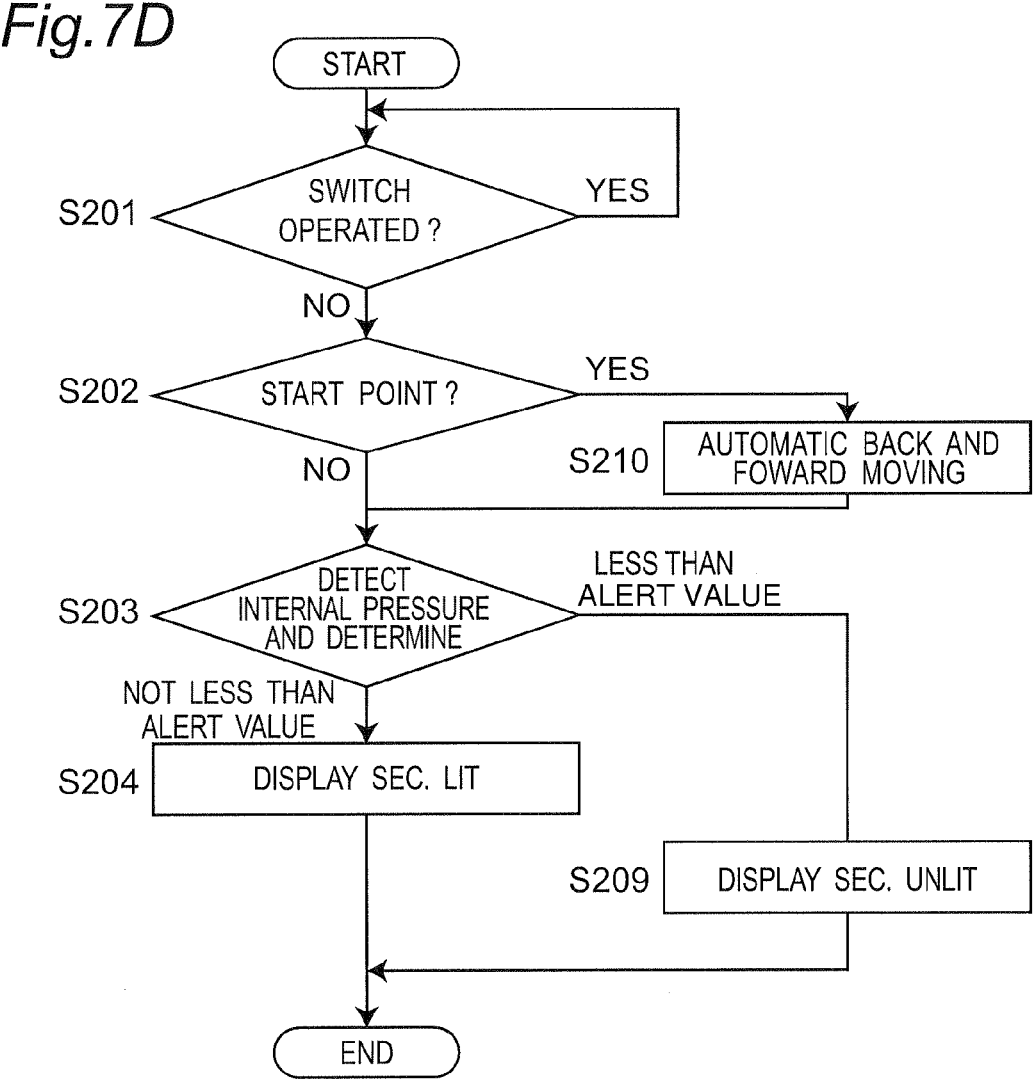
FIG. 7D is a flowchart of the operation steps in a non-automatic mode of the syringe drive device according to the first embodiment.
Figure 7E:
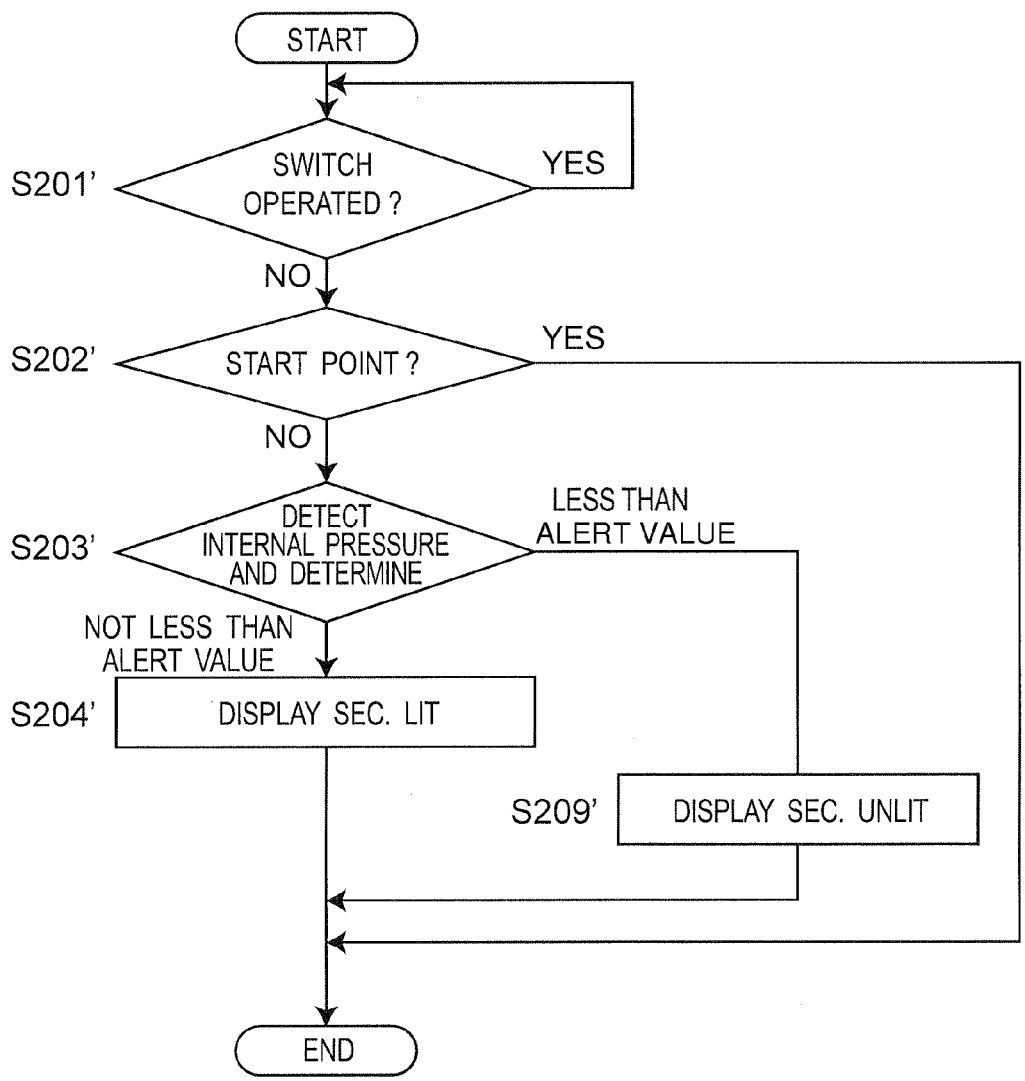
FIG. 7E is a flowchart of an alternative example of the operation steps in the non-automatic mode of the syringe drive device according to the first embodiment.
Figure 13:
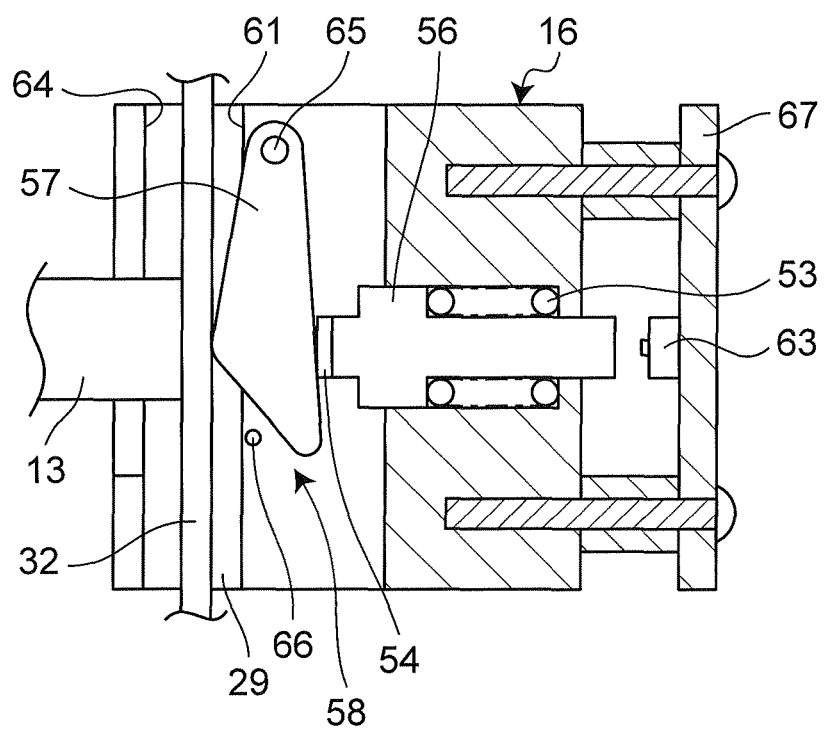
FIG. 13 is a sectional pattern view of a holder included in a syringe drive device according to a modification of the present invention.
Figure 14:
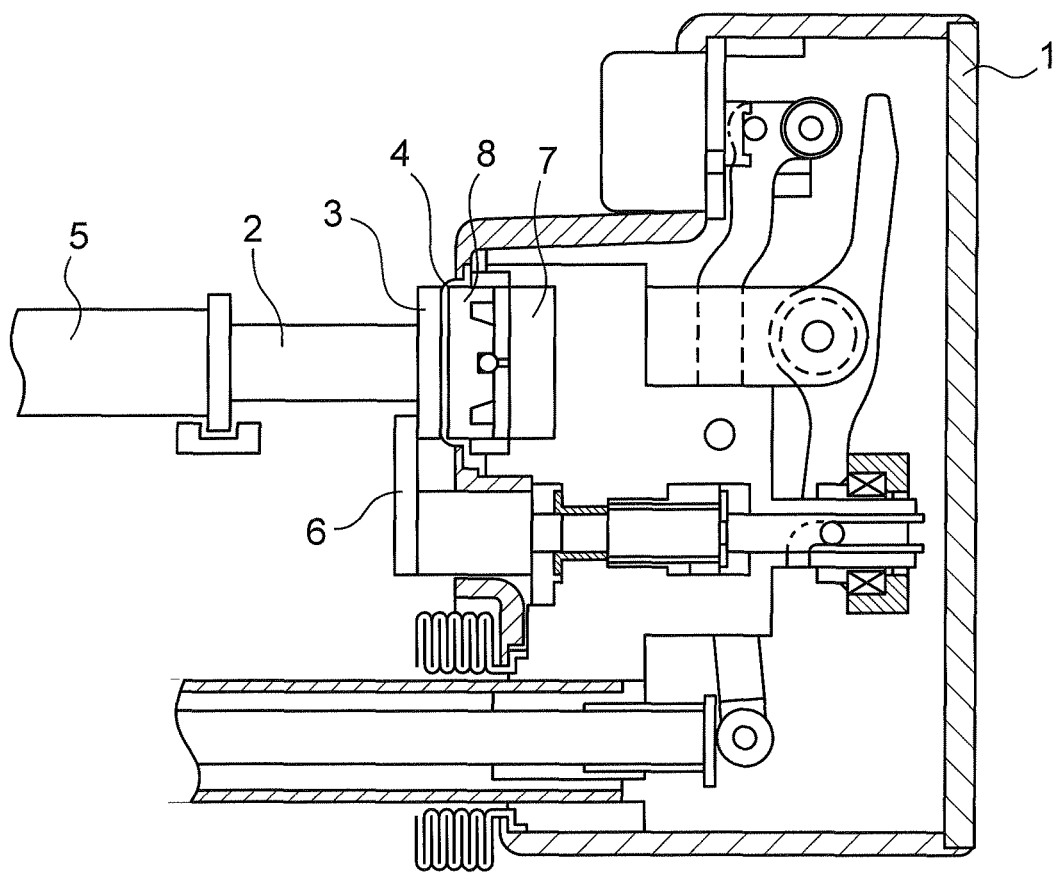
FIG. 14 is a sectional view of a main portion of a holder included in a conventional syringe drive device.

The present invention is not limited to the embodiments having been described, but can be modified in various ways. According to a modification shown in FIG. 13, in the syringe drive device 11 of the first embodiment in which the positive pressure detection switch 63 detecting the internal pressure of the syringe 12 as the ON/OFF state thereof is provided at the attachment member 67 so as to face the free piece 56, there is further provided the force sensor 54 at the distal end of the free piece 56 of the movable section 58. This force sensor 54 detects a force for pressing the free piece 56 so as to pull the plunger 13, by means of the press section 32 of the plunger 13 by way of the swing piece 57. The detection value of the force sensor 54 is inputted into the determination section 41. The determination section 41 is capable of calculating or estimating an appropriate distance of backward movement in accordance with the detection value of the force sensor 54 when the holder 16 (plunger 13) automatically moves backward (step S10 in FIG. 7A and step S210 in FIG. 7D) upon detection of the start point. The determination section 41 is also capable of calculating or estimating an appropriate distance of backward movement in accordance with the detection value of the force sensor 54 when the holder 16 (plunger 13) automatically moves backward (step S8 in FIG. 7A and step S8' in FIG. 7B) upon detection of a positive pressure in the automatic mode. In these cases, as the detection value of the force sensor 54 is larger, the distance of backward movement may be set longer. In particular, by calculating the distance of automatic backward movement of the holder 16 (plunger 13) upon detection of a positive pressure in the automatic mode in accordance with the detection value of the force sensor 54, the number of times of repetitive forward and backward movement (FIG. 7C) of the holder 16 can be reduced considerably. Reversely to the configuration shown in FIG. 13, the force sensor 54 may be provided at the attachment member 67 and the positive pressure detection switch 63 may be provided at the distal end of the free piece 56.

INDUSTRIAL APPLICABILITY

The syringe drive device and the method of controlling the syringe drive device according to the present invention realize alerting a user in advance to the occurrence of medicinal solution aerosolization, and are useful in operations of mixing injection drugs, in which a medicinal solution harmful to healthy people, such as a carcinostatic agent, is present.

The invention claimed is:

1. A method of driving a syringe that includes an outer tube fixing portion fixing an outer tube of the syringe, a holder holding a plunger of the syringe, and a drive portion driving the holder along an axis of the plunger to push and pull the plunger with respect to the outer tube, the method comprising:

detecting whether the holder is in a driven state or in a stopped state;
   detecting an internal pressure of the syringe when the holder is in the stopped state; and
   issuing an alert when the internal pressure of the syringe is not less than an alert value after the elapse of a predetermined standby period of time from said detecting of the stopped state of the holder.

2. A method of driving a syringe that includes an outer tube fixing portion fixing an outer tube of the syringe, a holder holding a plunger of the syringe, and a drive portion driving the holder along an axis of the plunger to push and pull the plunger with respect to the outer tube, the method comprising:
- detecting whether the holder is in a driven state or in a stopped state;
- detecting an internal pressure of the syringe when the holder is in the stopped state;
- determining whether or not the internal pressure of the syringe is not less than an alert value after the elapse of a predetermined standby period of time from said detecting of the internal pressure;
- issuing an alert when the internal pressure of the syringe is not less than an alert value; and
- when the internal pressure of the syringe is not less than the alert value, driving and moving the holder with the drive portion so as to pull the plunger out of the outer tube until the internal pressure of the syringe is reduced so as to be less than the alert value.

3. The method of claim 2, wherein the alert value is from 0 kPa to 5 kPa.

4. The method of claim 2, wherein, upon said detecting that the holder is in the stopped state, when the holder is located at a start point reached by the plunger being pushed to a limit toward the outer tube:
- moving the plunger so that the plunger is pulled out of the outer tube by a predetermined distance of backward movement,
- driving and moving the holder with the drive portion so as to push the plunger by a predetermined distance of forward movement, and
- then determining whether or not to issue the alert.

5. A method of driving a syringe that includes an outer tube fixing portion fixing an outer tube of the syringe, a holder holding a plunger of the syringe, and a drive portion driving the holder along an axis of the plunger to push and pull the plunger with respect to the outer tube, the method comprising:
- detecting that the holder is in a stopped state;
- detecting an internal pressure of the syringe with the holder in the stopped state; and
- determining that the internal pressure of the syringe is not less than an alert value after the elapse of a predetermined standby period of time from said detecting of the stopped state of the holder and then issuing an alert.

6. The method of claim 5, and further comprising driving and moving the holder with the drive portion so as to pull the plunger out of the outer tube until the internal pressure of the syringe is reduced so as to be less than the alert value.

7. The method of claim 5, wherein the alert value is from 0 kPa to 5 kPa.

8. The method of claim 5, wherein the holder is located at a start point reached by the plunger being pushed to a limit toward the outer tube, and further comprising:
- moving the plunger so that the plunger is pulled out of the outer tube by a predetermined distance of backward movement,
- driving and moving the holder with the drive portion so as to push the plunger by a predetermined distance of forward movement, and
- then determining whether or not to issue the alert.

* * * * *